United States Patent
Gross

(10) Patent No.: US 9,492,396 B2
(45) Date of Patent: Nov. 15, 2016

(54) ENHANCED DRUG DELIVERY PILL

(71) Applicant: RAINBOW MEDICAL LTD., Herzliya (IL)

(72) Inventor: Yossi Gross, Moshav Mazor (IL)

(73) Assignee: Yossi Gross, Moshav Mazor (IL)

( * ) Notice: Subject to any disclaimer, the term of this patent is extended or adjusted under 35 U.S.C. 154(b) by 0 days.

(21) Appl. No.: 14/319,808

(22) Filed: Jul. 15, 2014

(65) Prior Publication Data

US 2016/0015648 A1 Jan. 21, 2016

(51) Int. Cl.
*A61K 9/48* (2006.01)
*A61M 31/00* (2006.01)

(52) U.S. Cl.
CPC ............ *A61K 9/4808* (2013.01); *A61M 31/00* (2013.01)

(58) Field of Classification Search
CPC .... A61K 9/0065; A61K 9/48; A61K 9/4808; A61M 31/00
See application file for complete search history.

(56) References Cited

U.S. PATENT DOCUMENTS

| | | | |
|---|---|---|---|
| 4,767,627 A | 8/1988 | Caldwell et al. | |
| 4,878,905 A | 11/1989 | Blass | |
| 5,002,772 A | 3/1991 | Curatolo et al. | |
| 5,443,843 A | 8/1995 | Curatolo et al. | |
| 5,443,846 A | 8/1995 | Yoshioka et al. | |
| 5,637,319 A * | 6/1997 | Takada ................. | A61K 9/0004 424/451 |
| 6,235,313 B1 | 5/2001 | Mathiowitz et al. | |
| 6,245,057 B1 | 6/2001 | Sieben et al. | |
| 6,685,962 B2 | 2/2004 | Friedman et al. | |
| 6,958,034 B2 | 10/2005 | Iddan | |
| 6,994,095 B2 | 2/2006 | Burnett | |
| 7,009,634 B2 | 3/2006 | Iddan et al. | |
| 7,160,258 B2 | 1/2007 | Imran et al. | |
| 8,287,902 B2 | 10/2012 | Gross | |
| 8,295,932 B2 | 10/2012 | Bitton et al. | |

(Continued)

FOREIGN PATENT DOCUMENTS

| | | |
|---|---|---|
| WO | WO2004066903 | 8/2004 |
| WO | WO2005105053 | 11/2005 |

(Continued)

OTHER PUBLICATIONS

Email communication authorizing Examiner's Amendment—Jul. 8, 2016.*

(Continued)

*Primary Examiner* — Aradhana Sasan
(74) *Attorney, Agent, or Firm* — Sughrue Mion, PLLC

(57) ABSTRACT

An ingestible pill includes a coating configured to dissolve in a small intestine; a core, which includes a medication-delivery element, which (a) has a compressed shape when disposed within the coating, and (b) is configured to assume, after the coating dissolves, an expanded shape; a medication; and a mucoadhesive. When unconstrained in the expanded shape, the medication-delivery element (a) is shaped so as to define first and second surfaces on opposite sides of the medication-delivery element, which have respective outer perimeters, which surround respective spaces of the respective surfaces, which spaces have respective greatest dimensions equal to between 2 and 10 cm, and each of which spaces has an area equal to at least 50% of the square of the greatest dimension; and (b) has an average thickness between the first and the second surfaces of less than 6 mm. Each of the medication and the mucoadhesive at least partially coats the first surface.

29 Claims, 16 Drawing Sheets

(56) References Cited

U.S. PATENT DOCUMENTS

| | | |
|---|---|---|
| 8,414,559 B2 | 4/2013 | Gross |
| 2002/0082543 A1 | 6/2002 | Park et al. |
| 2003/0021845 A1 | 1/2003 | Friedman et al. |
| 2003/0153866 A1 | 8/2003 | Long et al. |
| 2004/0050394 A1 | 3/2004 | Jin |
| 2004/0162469 A1 | 8/2004 | Imran |
| 2004/0180086 A1 | 9/2004 | Ramtoola et al. |
| 2004/0253304 A1 | 12/2004 | Gross et al. |
| 2004/0267240 A1 | 12/2004 | Gross et al. |
| 2005/0055039 A1 | 3/2005 | Burnett et al. |
| 2005/0058701 A1 | 3/2005 | Gross et al. |
| 2006/0045865 A1 | 3/2006 | Jacob et al. |
| 2006/0142731 A1 | 6/2006 | Brooks |
| 2006/0178557 A1 | 8/2006 | Mintchev et al. |
| 2006/0276844 A1 | 12/2006 | Alon et al. |
| 2007/0005147 A1 | 1/2007 | Levine et al. |
| 2007/0156248 A1 | 7/2007 | Marco et al. |
| 2007/0250132 A1 | 10/2007 | Burnett |
| 2007/0293885 A1 | 12/2007 | Binmoeller |
| 2008/0063703 A1 | 3/2008 | Gross et al. |
| 2008/0188837 A1 | 8/2008 | Belsky et al. |
| 2008/0234834 A1 | 9/2008 | Meade et al. |
| 2008/0275430 A1 | 11/2008 | Belsky et al. |
| 2009/0247992 A1 | 10/2009 | Shalon et al. |
| 2010/0286628 A1 | 11/2010 | Gross |
| 2011/0066175 A1 | 3/2011 | Gross |
| 2011/0087195 A1 | 4/2011 | Uhland et al. |
| 2013/0274659 A1 | 10/2013 | Imran et al. |

FOREIGN PATENT DOCUMENTS

| | | |
|---|---|---|
| WO | WO2007007339 | 1/2007 |
| WO | WO2007086078 | 8/2007 |
| WO | WO2008023374 | 2/2008 |
| WO | WO2008121409 | 10/2008 |
| WO | WO2008121831 | 10/2008 |
| WO | WO2008154450 | 12/2008 |
| WO | WO2010128495 | 11/2010 |
| WO | WO2011151830 | 12/2011 |

OTHER PUBLICATIONS

Interview Agenda for May 17, 2016.*
Klausner et al., "Expandable Gastroretentive Dosage Forms", Journal of Controlled Release 90 (2003) 143-162.
Medimetrics IntelliCap webpage, MediMetrics, downloaded Feb. 23, 2014.
Tao et al., "Gastrointestinal patch systems for oral drug delivery," Drug Discovery Today, vol. 10(13), Jul. 2005.
Wen MM, "Advances and Challenges in the Dosage Form Design for the Treatment of Parkinson's Disease," Discovery Medicine, Dec. 24, 2012.

* cited by examiner

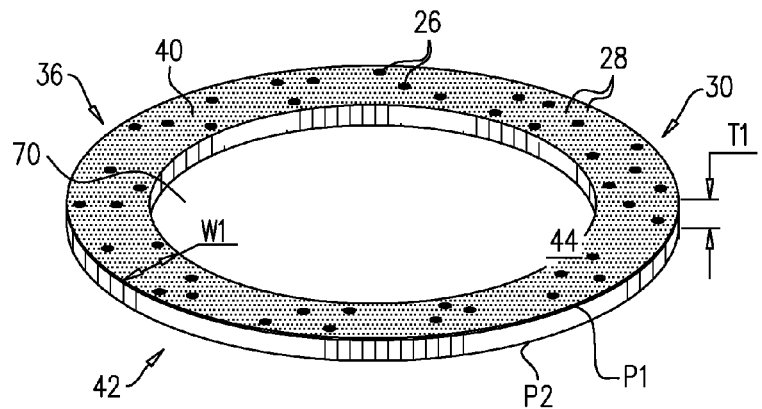
FIG. 3A
FIG. 3B
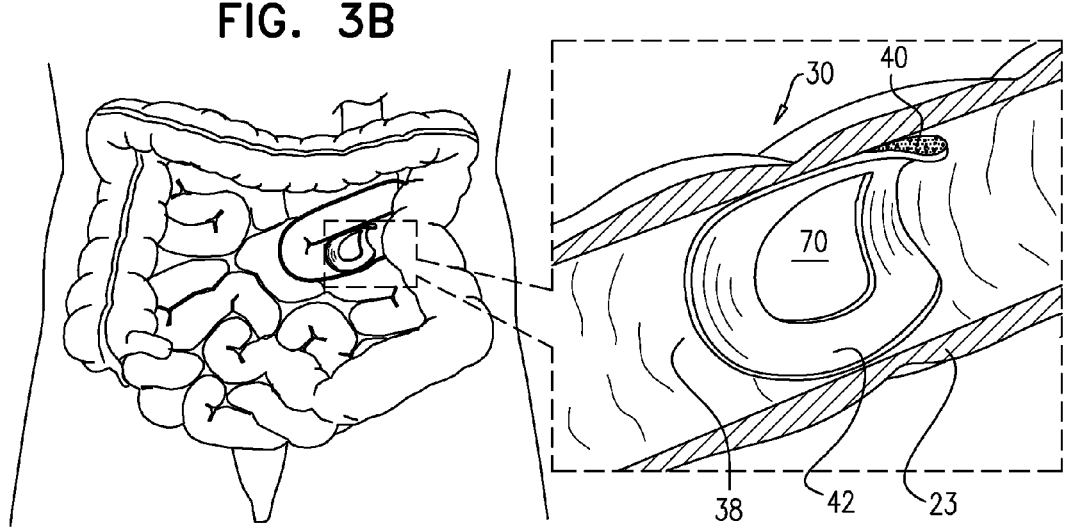
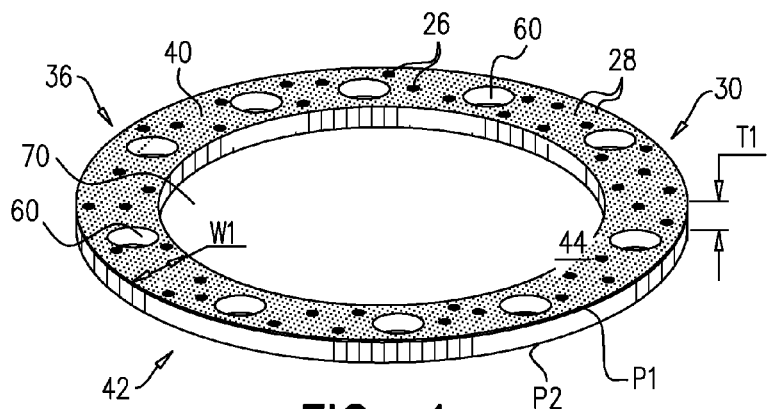
FIG. 4

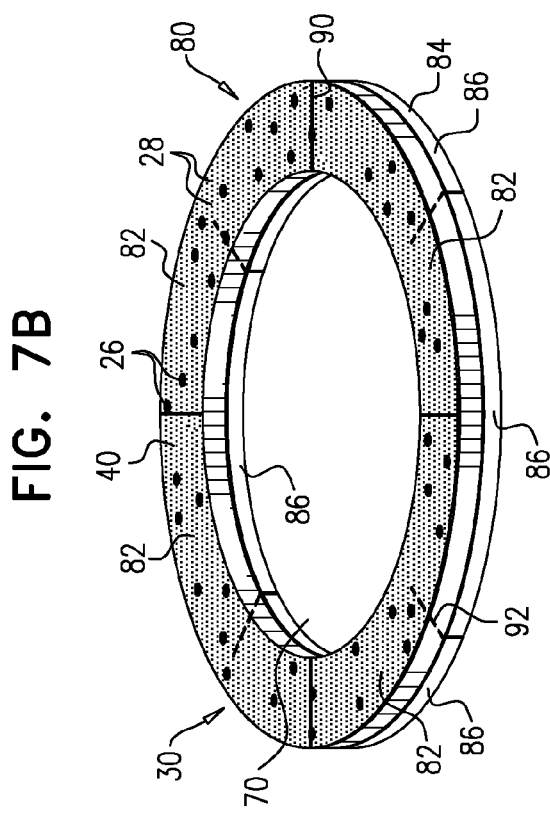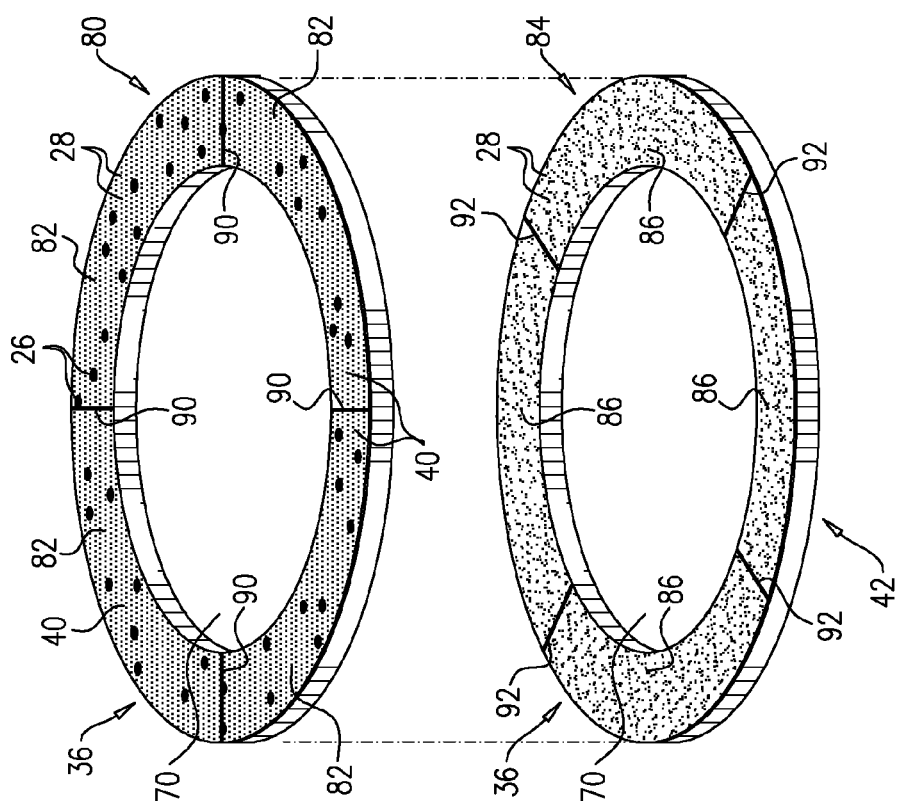

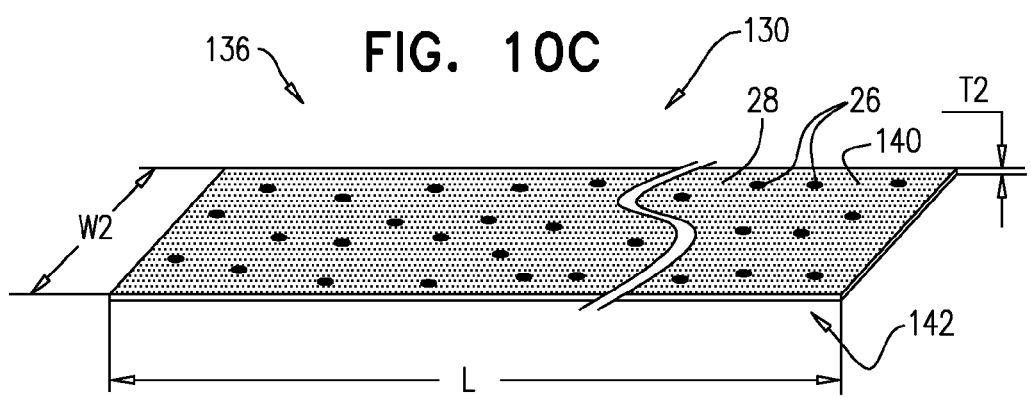
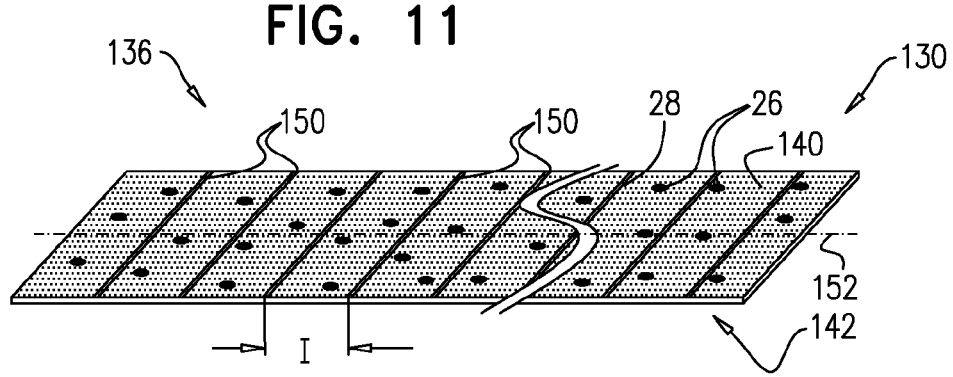

ENHANCED DRUG DELIVERY PILL

FIELD OF THE INVENTION

The present invention generally relates to medical apparatus. Specifically, the present invention relates to an ingestible capsule for administering medication to a subject.

BACKGROUND OF THE INVENTION

Medication is frequently stored in a capsule and administered to a subject who swallows the capsule. The medication passes through the intestinal wall and enters the blood of the subject.

U.S. Pat. No. 8,287,902 to Gross, which is incorporated herein by reference, describes an ingestible capsule for delivering medication to a subject. A capsule coating dissolves in a gastrointestinal tract of the subject. An inner core of the capsule has an outer surface associated therewith. The outer surface is disposed within the coating and expands when the coating dissolves. A medication is disposed on the outer surface, and the outer surface is configured such that the medication contacts an intestinal wall of the subject when the outer surface expands.

SUMMARY OF APPLICATIONS

Some embodiments of the present invention provide ingestible pills that comprise a coating, a core, a medication, and, optionally, a mucoadhesive. In accordance with different applications of the present invention, the core comprises various medication-delivery elements which are configured to make good contact with the wall of the small intestine in order to bring the medication into good contact with the intestinal wall and effectively deliver the medication through the intestinal wall. In general, the medication-delivery elements described herein utilize shape, size, and mechanical properties to cause a desired orientation of the elements in the small intestine that provides good contact of a medication-coated surface of the element with the intestinal wall.

In some applications of the present invention, establishing good contact between the medication and the intestinal wall allows oral administration of large molecules which generally have low availability via oral delivery when contact between the medication and the wall of the intestine is not established. Typically, the medication is in powder or gel form, and diffuses rapidly through the intestinal wall in response to the high concentration of the medication and the complete or nearly complete contact with the intestinal wall of an expanded surface of the drug-delivery element.

In some applications of the present invention, the core comprises a medication-delivery element, which has a compressed shape when disposed within the coating, and is configured to assume an expanded shape after the coating dissolves. For some applications, the medication-delivery element is rolled when in the compressed shape within the coating. When unconstrained in the expanded shape, the medication-delivery element: (a) is shaped so as to define first and second surfaces on opposite sides of the medication-delivery element, and (b) has an average thickness of an edge between the first and second surfaces of between 1 and 6 mm. The first and second surfaces and have respective outer perimeters, which surround respective spaces of the respective surfaces. The spaces have respective greatest dimensions equal to between 2 and 10 cm. Typically, each of the greatest dimensions is slightly larger than the circumference of the small intestine, such that when the medication-delivery element is in the expanded shape, it generally presses outward against the intestinal wall. Each of the spaces has an area equal to at least 50% of the square of the greatest dimension of the space, such as at least 75% of the square of the greatest dimension.

Each of the medication and the mucoadhesive at least partially coats the first surface. The mucoadhesive transiently adheres the first surface in position against the intestinal wall during delivery of the medication through the intestinal wall. For some applications, the first and second surfaces are circular.

The medication-delivery element expands, such as by stretching, unfolding, and/or unrolling, in response to no longer being constrained by the coating, and/or in response to contact of the core with fluid in the small intestine. Once expanded, the first surface establishes good (complete or nearly complete) contact with intestinal wall. Factors contributing to this good contact include: (a) the shape and dimensions of the medication-delivery element, which prevent other, lower-contact-level orientations of the element in the lumen of the small intestine, and (b) the disposition of the mucoadhesive on the first surface, which holds the expanded first surface in position during delivery of the medication. Because of this good contact, the medication disposed on the first surface typically makes contact with the intestinal wall, enhancing diffusion of the medication through the wall. This good contact, typically in combination with the high concentration of the medication on the first surface, results in delivery of a high quantity of the medication through the intestinal wall. Following delivery of the medication, the core, including the medication-delivery element, is passed from the body.

For some applications, the medication-delivery element, when unconstrained in the expanded shape, is shaped so as to define a plurality of openings therethrough. These openings may allow for high compression of the medication-delivery element when in the compressed shape when disposed within the coating, while still providing good contact with the intestinal wall of the portion of the first surface that is coated with the medication. Providing the openings thus does not necessarily decrease the total drug-coated surface area that contacts the intestinal wall. For some applications, when the medication-delivery element is unconstrained in the expanded shape, an aggregate area of the openings equals at least 10% (e.g., at least 30%) of the area of the space surrounded by the outer perimeter of the first surface. Alternatively or additionally, an average area of the openings equals at least 0.5% (e.g., at least 1%) of the area of the space.

For some applications, the medication-delivery element, when unconstrained in the expanded shape (as shown), is shaped so as to define an opening therethrough. This opening may allow for high compression of the medication-delivery element when in the compressed shape when disposed within the coating, while still providing good contact of the first surface with the intestinal wall for drug delivery when the medication-delivery element is in the expanded shape. For some applications, when the medication-delivery element is unconstrained in the expanded shape, an area of the opening equals between 25% and 90% of the area of the space surrounded by the outer perimeter of the first surface. Alternatively or additionally, for some applications, the area of the opening is at least 2.5 cm2. For some applications, the medication-delivery element is shaped so as to define only a single opening, and no other openings.

For some applications, the medication-delivery element is shaped as a ring around the opening, when the medication-delivery element is unconstrained in the expanded shape. For these applications, the medication-delivery element may be considered to be shaped as an annulus, such as a thin annulus. For some applications, the outer perimeter of the ring is between 6 and 30 cm.

For some applications, when the medication-delivery element is unconstrained in the expanded shape, an average width of the medication-delivery element, measured between the outer perimeter of the first surface and the opening, equals between 3 and 8 times the average thickness, and/or equals between 3 and 12 mm. This relatively large width facilitates proper alignment of the medication-delivery element around the wall of the small intestine. In contrast, if shaped as a conventional o-ring, and with no further modifications, the medication-delivery element would not align properly against the wall of the small intestine.

For some applications, the medication-delivery element is configured to break apart in the small intestine.

In some applications of the present invention, the core comprises an elongate medication-delivery element shaped as a ribbon. The elongate medication-delivery element (a) has a compressed shape when disposed within the coating, (b) is configured to assume, after the coating dissolves, an expanded shape, (c) comprises the medication, and (d) typically has a thickness of less than 0.5 mm, a length of between 10 and 50 cm, and a width of between 0.5 and 3 cm. The elongate medication-delivery element is configured such that the medication contacts the intestinal wall when the elongate medication-delivery element has the expanded shape.

The elongate medication-delivery element is shaped so as to define first and second surfaces on opposite sides of the elongate medication-delivery element. The medication at least partially coats the first surface. For some applications, the pill further comprises the mucoadhesive, which at least partially coats the first surface. For some applications, the medication is disposed along at least 75% of a length of the elongate medication-delivery element, measured along a longitudinal axis of the elongate medication-delivery element.

For some applications, the elongate medication-delivery element is rolled when in the compressed shape when disposed within the coating. For applications in which the mucoadhesive is disposed only on the first surface, rolling the element prevents the mucoadhesive from adhering to itself between turns of the rolled element. Alternatively, the elongate medication-delivery element is folded, e.g., in a zigzag shape, a serpentine shape, or a sinusoidal shape, when in the compressed shape when disposed within the coating.

The elongate medication-delivery element expands, such as by unrolling and/or unfolding, in response to no longer being constrained by the coating, and/or in response to contact of the core with fluid in the small intestine. Natural peristalsis may aid in such unrolling or unfolding. Once expanded, the first surface establishes good (complete or nearly complete) contact with the intestinal wall. Factors contributing to this good contact include: (a) the shape and dimensions of the medication-delivery element, which prevent other, lower-contact-level orientations of the element in the lumen of the small intestine, and (b) the disposition of the mucoadhesive on the first surface, which holds the expanded first surface in position during delivery of the medication, in applications in which the mucoadhesive is provided. Because of this good contact, the medication disposed on the first surface typically makes contact with the intestinal wall. This good contact, typically in combination with the high concentration of the medication on the first surface, results in delivery of a high quantity of the medication through the intestinal wall. Typically, peristalsis has little effect on the elongate medication-delivery element. Following delivery of the medication, the core, including the elongate medication-delivery element, is passed from the body.

For some applications, the pill further comprises sodium bicarbonate, which at least partially coats at least one of the first and second surfaces. Upon dissolving of the coating, the sodium bicarbonate continuously becomes moist, and releases a gas that promotes unrolling of the elongate medication-delivery element.

For some applications, the elongate medication-delivery element has a plurality of ribs. The ribs may help avoid random twisting of the elongate medication-delivery element as it unrolls in the small intestine. Optionally, the ribs are arched. For some applications, the ribs are formed by a thickening of the material of the elongate medication-delivery element, while for other applications, the ribs comprise a material that is fixed to the first surface and/or second surface of the elongate medication-delivery element. For some applications, the ribs are arranged perpendicular to the longitudinal axis of the elongate medication-delivery element, at intervals along the element.

For some applications, the elongate medication-delivery element is inflatable, and is configured to transition from the compressed shape to the expanded shape upon inflation. Inflation of the elongate medication-delivery element transitions the element to the expanded shape, such as by unrolling (and/or unfolding). For some applications, the elongate medication-delivery element deflates soon after unrolling, and assumes a shape that is flat and non-circular in cross-section. For some applications, the ribs facilitate such deflation.

In some applications of the present invention, the core comprises an elongate medication-delivery element having an outer surface and a longitudinal axis. The elongate medication-delivery element (a) has a compressed shape when disposed within the coating, (b) is configured to assume, after the coating dissolves, an expanded shape of a three-dimensional space curve, and (c) comprises the medication. The outer surface is configured such that the medication contacts the intestinal wall when the elongate medication-delivery element has the expanded shape.

For some applications, at least 50% of a length of the elongate medication-delivery element is shaped as a helix when the elongate medication-delivery element has the expanded shape and is unconstrained. For some applications, the helix is a circular helix when the elongate medication-delivery element has the expanded shape and is unconstrained. For some applications, the helix has an outer diameter of between 4 and 7 cm when the elongate medication-delivery element has the expanded shape and is unconstrained.

The elongate medication-delivery element expands, such as by unfolding and/or unrolling, in response to no longer being constrained by the coating, and/or in response to contact of the core with fluid in the small intestine. Natural peristalsis may aid in such unrolling or unfolding. Once expanded, a radially-outwardly-directed portion of the outer surface establishes good (complete or nearly complete) contact with the intestinal wall. Factors contributing to this good contact include: (a) the shape and dimensions of the medication-delivery element, which prevent other, lower-contact-level orientations of the element in the lumen of the small intestine, and (b) the disposition of the mucoadhesive on the radially-outwardly-directed portion of the outer surface, which holds the radially-outwardly-directed portion of the expanded the outer surface in position during delivery of the medication, in applications in which the mucoadhesive is provided. Because of this good contact, the medication disposed on the radially-outwardly-directed portion of the outer surface typically makes contact with the intestinal wall. This good contact, typically in combination with the high concentration of the medication on the outer surface, results in delivery of a high quantity of the medication through the intestinal wall. Following delivery of the medication, the core, including the elongate medication-delivery element, is passed from the body.

In some applications of the present invention, the core comprises a sponge, which (a) has a compressed shape and compressed volume when disposed within the coating, (b) is configured to assume, after the coating dissolves, an expanded shape and an expanded volume, the expanded volume at least 3 times (such as at least 5 times) the compressed volume, and (c) comprises the medication and the mucoadhesive.

For some applications, the mucoadhesive is disposed on a portion of an outer surface of the sponge, which outer surface is configured such that the mucoadhesive contacts the intestinal wall when the sponge has the expanded shape. Alternatively or additionally, for some applications, the medication is disposed on at least a portion of the outer surface of the sponge, which outer surface is configured such that the medication contacts the intestinal wall when the sponge has the expanded shape. For some applications, when the sponge has the expanded shape and is unconstrained, the outer surface of the sponge has a surface area, and the medication is disposed on less than 50% of the surface area.

In some applications of the present invention, the core comprises a medication-delivery ring, which (a) has a compressed shape when disposed within the coating, (b) is configured to assume, after the coating dissolves, an expanded shape, and (c) comprises the medication. When the medication-delivery ring is unconstrained in the expanded shape, the medication-delivery ring has (a) an outer perimeter of between 6 and 30 cm, and (b) a thickness, measured in a direction perpendicular to a plane defined by the outer perimeter, of less than 0.5 cm. The medication-delivery ring is configured such that the medication contacts the intestinal wall when the medication-delivery ring has the expanded shape.

The relatively flat and large shape of the medication-delivery ring results in the ring wrapping around a portion of the intestinal wall, with good contact with the wall. In contrast, if shaped as a conventional o-ring, and with no further modifications, medication-delivery element 330 would not align properly against the wall of the small intestine.

For some applications, when the medication-delivery ring is unconstrained in the expanded shape, an average width of the medication-delivery ring, measured between the outer perimeter of the medication-delivery ring and an inner perimeter of the medication-delivery ring, equals between 3 and 8 times the thickness.

For some applications, the medication-delivery ring is inflatable and is shaped so as to define at least one internal chamber. The medication-delivery ring is uninflated when in the compressed shape when disposed within the coating, and the medication-delivery ring is configured to assume the expanded shape upon inflation. For some applications, the medication-delivery ring comprises radial ribs, which are configured to prevent over-inflation.

For some applications, the medication-delivery ring further comprises sodium bicarbonate, and a substance, such as an acid (e.g., citric acid), or water, typically disposed in the at least one internal chamber.

There is therefore provided, in accordance with an application of the present invention, apparatus including an ingestible pill, which includes:

a coating configured to dissolve in a small intestine of a subject;

a core, which includes a medication-delivery element, which (a) has a compressed shape when disposed within the coating, and (b) is configured to assume, after the coating dissolves, an expanded shape;

a medication; and a mucoadhesive, wherein, when the medication-delivery element is unconstrained in the expanded shape:

the medication-delivery element is shaped so as to define first and second surfaces on opposite sides of the medication-delivery element, which first and second surfaces have respective outer perimeters, which surround respective spaces of the respective surfaces, which spaces have respective greatest dimensions equal to between 2 and 10 cm, and each of which spaces has an area equal to at least 50% of the square of the greatest dimension thereof, and the medication-delivery element has an average thickness between the first and the second surfaces of less than 6 mm, wherein each of the medication and the mucoadhesive at least partially coats the first surface.

For some applications, the area of each of the spaces is equal to at least 75% of the square of the greatest dimension thereof.

For some applications, the greatest dimensions are at least 3 cm, such as at least 4 cm.

For some applications, the greatest dimensions are no more than 7 cm.

For some applications, the medication-delivery element, when unconstrained in the expanded shape, is generally flat.

For some applications, the medication-delivery element, when unconstrained in the expanded shape, is curved out of plane.

For some applications, at least 90% of the mucoadhesive, by weight, is disposed on the first surface.

For some applications, less than 10% of the mucoadhesive, by weight, is disposed on the second surface.

For some applications, at least 90% of the medication, by weight, is disposed on the first surface.

For some applications, less than 10% of the medication, by weight, is disposed on the second surface.

For some applications, at least 75% of the first surface faces at least partially radially outwardly, when the medication-delivery element has the compressed shape when disposed within the coating. For some applications, at least 90% of the medication, by weight, is disposed on the first surface. For some applications, less than 10% of the medication, by weight, is disposed on the second surface.

For some applications, the second surface is generally impermeable to the medication.

For some applications, the first and the second surfaces are circular, and the greatest dimensions are respective diameters of the first and the second surfaces.

For some applications, the first and the second surfaces are rectangular, and the greatest dimensions are respective diagonals of the first and the second surfaces.

For some applications, the first and the second surfaces are polygonal.

For some applications, the first and the second surfaces are elliptical.

For some applications, the mucoadhesive is arranged as dots on the first surface.

For some applications, the mucoadhesive is mixed with the medication.

For some applications, the average thickness is at least 1 mm when the medication-delivery element is unconstrained in the expanded shape.

For some applications, the average thickness is less than 4 mm when the medication-delivery element is unconstrained in the expanded shape.

For some applications, 90% of the mucoadhesive is disposed within a distance of a perimeter of the first surface, which distance equals 25% of the greatest dimension of the first surface.

For some applications, 90% of the medication is disposed more than a distance from the perimeter, which distance equals 25% of the greatest dimension of the first surface.

For some applications, the medication-delivery element includes an elastomer. For some applications, the elastomer includes silicone.

For some applications, the medication-delivery element includes a sponge.

For some applications, the pill includes a shell, which includes the coating.

For some applications, the core is directly coated with the coating.

For some applications, the pill has a length of between 5 and 30 mm before the coating dissolves.

For some applications, the medication is disposed on the first surface so as to define a plurality of protrusions, each of which has a length of between 50 and 400 microns. For some applications, a greatest radius of each of the protrusions is between 20 and 100 microns.

For some applications, the medication-delivery element includes one or more threads, which are configured to intertwine with villi of the small intestine. For some applications, each of at least 90% of the threads has a diameter of between 20 and 50 microns. For some applications, each of at least 90% of the threads has a length of between 1 and 10 cm. For some applications, each of at least 90% of the threads has a length of between 10 and 50 cm. For some applications, the threads are biodegradable.

For some applications, the coating is pH-sensitive, and is configured to dissolve within 10 minutes only within a range of pH values, which range has a low end of between 6.5 and 8.5.

For some applications, the medication-delivery element includes a biodegradable polymer mixed with a flexible material.

For any of the previous applications, the medication-delivery element, when unconstrained in the expanded shape, may be shaped so as to define one or more openings therethrough. For some applications, the medication-delivery element, when unconstrained in the expanded shape, is shaped so as to define a plurality of openings therethrough. For some applications, an aggregate area of the plurality of openings equals at least 10% of the area of the space surrounded by the outer perimeter of the first surface, when the medication-delivery element is unconstrained in the expanded shape. For some applications, the aggregate area of the plurality of openings equals between 10% and 60% of the area of the space surrounded by the outer perimeter of the first surface, when the medication-delivery element is unconstrained in the expanded shape. For some applications, the aggregate area of the plurality of openings is no more than 60% of the area of the space surrounded by the outer perimeter of the first surface, when the medication-delivery element is unconstrained in the expanded shape. For some applications, the aggregate area of the plurality of openings equals at least 30% of the area of the space surrounded by the outer perimeter of the first surface, when the medication-delivery element is unconstrained in the expanded shape.

For some applications, an average area of the plurality of openings equals at least 0.5% of the area of the space surrounded by the outer perimeter of the first surface, when the medication-delivery element is unconstrained in the expanded shape. For some applications, the average area of the plurality of openings equals no more than 10% of the area of the space surrounded by the outer perimeter of the first surface, when the medication-delivery element is unconstrained in the expanded shape.

For some applications, an average area of the plurality of openings equals between 1 and 50 mm2. For some applications, an average area of the plurality of openings equals between 1 and 5 mm2. For some applications, an average area of the plurality of openings equals between 5 and 12 mm2. For some applications, an average area of the plurality of openings equals between 12 and 50 mm2.

For some applications, an area of one of the one or more openings equals between 25% and 90% of the area of the space surrounded by the outer perimeter of the first surface, when the medication-delivery element is unconstrained in the expanded shape. For some applications, the area of the one of the one or more openings equals between 50% and 85% of the area of the space surrounded by the outer perimeter of the first surface, when the medication-delivery element is unconstrained in the expanded shape. For some applications, the area of the one of the one or more openings is at least 2.5 cm2. For some applications, the medication-delivery element is circular, and the greatest dimension is a diameter of the medication-delivery element, when the medication-delivery element is unconstrained in the expanded shape.

For some applications, the one or more openings include the one opening and a plurality of second openings, and an average area of the second openings equals between 1% and 10% of the area of the space surrounded by the outer perimeter of the first surface, when the medication-delivery element is unconstrained in the expanded shape. For some applications, the average area of the second openings equals between 2% and 5% of the area of the space surrounded by the outer perimeter of the first surface, when the medication-delivery element is unconstrained in the expanded shape.

For some applications, the one or more openings includes only the one opening. For some applications, the medication-delivery element is shaped as a ring around the one opening, when the medication-delivery element is unconstrained in the expanded shape.

For some applications, the medication-delivery element is shaped as a ring around the one of the one or more openings, when the medication-delivery element is unconstrained in the expanded shape.

For some applications, an average width of the medication-delivery element, measured between the outer perimeter of the first surface and the one of the one or more openings, equals at least 3 times the average thickness, when the medication-delivery element is unconstrained in the expanded shape.

For some applications, an average width of the medication-delivery element, measured between the outer perimeter of the first surface and the one of the one or more openings, equals at least 3 mm, when the medication-delivery element is unconstrained in the expanded shape.

For some applications, the average thickness is at least 0.5 mm. For some applications, the average thickness is between 0.5 and 3 mm.

For some applications, the medication-delivery element includes an elastomer. For some applications, the elastomer includes silicone.

For some applications, when the medication-delivery element has the compressed shape, the medication-delivery element is in a folded configuration that is rolled.

For some applications, when the medication-delivery element has the compressed shape, the medication-delivery element is in a folded configuration that is twisted.

For some applications, the medication-delivery element is configured to break apart in the small intestine. For some applications, the medication-delivery element includes:
a first layer, which defines the first surface, and which includes a plurality of first pieces;
a second layer, which defines the second surface, and which includes a plurality of second pieces; and
a material that is biodegradable in the small intestine, and couples the first and the second layers to one another,
wherein, when the first and the second layers are coupled to one another:
the first pieces are arranged such that they adjoin each other at respective first interfaces,
the second pieces are arranged such that they adjoin each other at respective second interfaces, and
the first and the second pieces are arranged such that the first interfaces are offset from the second interfaces.

For some applications, when the first and the second layers are coupled to one another, the first and the second pieces are arranged such that the first interfaces are rotationally offset from the second interfaces.

For some applications, the material includes a glue, which is spread between the first and the second layers.

For some applications, the first and the second layers are shaped so as to define a plurality of corresponding holes, and the material is shaped as a plurality of pegs, each of which is disposed in a pair of corresponding holes defined by the first and the second layers, respectively.

For any of the previous applications, a non-border area of the medication-delivery element may be shaped to define a cut-out flap that includes respective portions of the first and the second surfaces, each of which portions has an area of at least 1 cm2. For some applications, the medication is disposed on a free edge of the flap.

There is further provided, in accordance with an application of the present invention, a method including:
receiving, by a subject, an ingestible pill, which includes (i) a coating configured to dissolve in a small intestine of the subject, and (ii) a core, which includes a medication-delivery element, which (a) has a compressed shape when disposed within the coating, and (b) is configured to assume, after the coating dissolves, an expanded shape, (iii) a medication, and (iv) a mucoadhesive; and
swallowing the ingestible pill by the subject, so that the coating dissolves in the small intestine and the medication-delivery element assumes the expanded shape,
wherein, when the medication-delivery element is unconstrained in the expanded shape:
the medication-delivery element is shaped so as to define first and second surfaces on opposite sides of the medication-delivery element, which first and second surfaces have respective outer perimeters, which surround respective spaces of the respective surfaces, which spaces have respective greatest dimensions equal to between 2 and 10 cm, and each of which spaces has an area equal to at least 50% of the square of the greatest dimension thereof, and
the medication-delivery element has an average thickness between the first and the second surfaces of less than 6 mm,
wherein each of the medication and the mucoadhesive at least partially coats the first surface.

There is still further provided, in accordance with an application of the present invention, apparatus including an ingestible pill, which includes:
a coating configured to dissolve in a small intestine of a subject; and
a core, which includes an elongate medication-delivery element shaped as a ribbon, wherein the elongate medication-delivery element (a) has a compressed shape when disposed within the coating, (b) is configured to assume, after the coating dissolves, an expanded shape, (c) includes a medication, and (d) has a thickness of less than 0.5 mm, a length of between 10 and 50 cm, and width of between 0.5 and 3 cm,
wherein the elongate medication-delivery element is configured such that the medication contacts an intestinal wall of the subject when the elongate medication-delivery element has the expanded shape.

For some applications, the elongate medication-delivery element has a plurality of ribs. For some applications, the ribs are arranged perpendicular to a longitudinal axis of the elongate medication-delivery element.

For some applications, the elongate medication-delivery element includes a material selected from the group of materials consisting of: starch and gelatin.

For some applications, the thickness of the elongate medication-delivery element is less than 0.1 mm.

For some applications, the medication is disposed along at least 75% of a length of the elongate medication-delivery element, measured along a longitudinal axis of the elongate medication-delivery element.

For some applications, the pill has a length of between 5 and 30 mm before the coating dissolves.

For some applications, the compressed shape is selected from the group of shapes consisting of: a serpentine shape, a sinusoidal shape, and a zigzag shape.

For some applications, the pill includes a shell, which includes the coating.

For some applications, the core, when disposed within the coating, is directly coated with the coating.

For some applications, the elongate medication-delivery element is biodegradable.

For some applications, the medication is disposed on the elongate medication-delivery element so as to define a plurality of protrusions, each of which has a length of between 50 and 300 microns, such as between 20 and 100 microns.

For some applications, the elongate medication-delivery element includes one or more threads, which are configured to intertwine with villi of the small intestine. For some applications, each of at least 90% of the threads has a diameter of between 20 and 50 microns. For some applications, each of at least 90% of the threads has a length of between 1 and 10 cm. For some applications, each of at least 90% of the threads has a length of between 10 and 50 cm. For some applications, the threads are biodegradable.

For some applications, the medication includes a powder.

For some applications, the coating includes a gelatin coating configured to constrain the elongate medication-delivery element from expanding before the gelatin coating dissolves.

For some applications, the pill further includes a chemical enhancer configured to enhance delivery of the medication to the subject.

For some applications, the chemical enhancer includes lipophilic molecules configured to enhance diffusion of the medication through an epithelial layer of the intestinal wall of the subject.

For some applications, the coating is pH-sensitive, and is configured to dissolve within 10 minutes only within a range of pH values, which range has a low end of between 6.5 and 8.5.

For any of the previous applications, the elongate medication-delivery element may be shaped so as to define first and second surfaces on opposite sides of the elongate medication-delivery element, and the medication at least partially coats the first surface. For some applications, the pill further includes a mucoadhesive, which at least partially coats the first surface. For some applications, the pill further includes sodium bicarbonate, which at least partially coats at least one of the first and the second surfaces. For some applications, the pill further includes silicone, which at least partially coats the second surface.

For any of the previous applications, the elongate medication-delivery element may be rolled when the elongate medication-delivery element has the compressed shape when disposed within the coating. For some applications, the elongate medication-delivery element is inflatable, and is configured to transition from the compressed shape to the expanded shape upon inflation. For some applications, the elongate medication-delivery element includes one or more elongate dividers aligned longitudinally along the elongate medication-delivery element, which at least partially divide an interior of the inflatable elongate medication-delivery element into a plurality of longitudinal chambers.

There is additionally provided, in accordance with an application of the present invention, a method including:

receiving, by a subject, an ingestible pill, which includes (i) a coating configured to dissolve in a small intestine of the subject, and (ii) a core, which includes an elongate medication-delivery element shaped as a ribbon, wherein the elongate medication-delivery element (a) has a compressed shape when disposed within the coating, (b) is configured to assume, after the coating dissolves, an expanded shape, (c) includes a medication, and (d) has a thickness of less than 0.5 mm, a length of between 10 and 50 cm, and width of between 0.5 and 3 cm; and swallowing the ingestible pill by the subject, so that the coating dissolves in the small intestine, the elongate medication-delivery element assumes the expanded shape, and the medication contacts an intestinal wall of the subject when the elongate medication-delivery element has the expanded shape.

There is yet additionally provided, in accordance with an application of the present invention, apparatus including an ingestible pill, which includes:

a coating configured to dissolve in a small intestine of a subject; and a core, which includes an elongate medication-delivery element having an outer surface and a longitudinal axis, wherein the elongate medication-delivery element (a) has a compressed shape when disposed within the coating, (b) is configured to assume, after the coating dissolves, an expanded shape of a three-dimensional space curve, and (c) includes a medication, wherein the outer surface is configured such that the medication contacts an intestinal wall of the subject when the elongate medication-delivery element has the expanded shape.

For some applications, the elongate medication-delivery element includes a sponge. For some applications, the medication includes a liquid that is absorbed in the sponge.

For some applications, the pill further includes a mucoadhesive coated on a portion of the outer surface of the elongate medication-delivery element. For some applications, the mucoadhesive is mixed with the medication.

For some applications, the elongate medication-delivery element has a length, measured along the longitudinal axis of the elongate medication-delivery element, of between 10 and 50 cm when the elongate medication-delivery element has the expanded shape and is unconstrained.

For some applications, the elongate medication-delivery element has an average cross-sectional area perpendicular to the longitudinal axis of the elongate medication-delivery element of between 7 and 80 mm2 when the elongate medication-delivery element has the expanded shape and is unconstrained. For some applications, the elongate medication-delivery element has a length, measured along the longitudinal axis of the elongate medication-delivery element, of between 10 and 50 cm when the elongate medication-delivery element has the expanded shape and is unconstrained.

For some applications, the medication is disposed along at least 75% of a length of the elongate medication-delivery element, measured along the longitudinal axis of the elongate medication-delivery element, when the elongate medication-delivery element has the expanded shape and is unconstrained.

For some applications, the elongate medication-delivery element has a non-circular cross-sectional shape perpendicular to the longitudinal axis of the elongate medication-delivery element when the elongate medication-delivery element has the compressed shape, and a circular cross-sectional shape perpendicular to the longitudinal axis of the elongate medication-delivery element when the elongate medication-delivery element has the expanded shape and is unconstrained. For some applications, the elongate medication-delivery element has an elliptical cross-sectional shape perpendicular to the longitudinal axis of the elongate medication-delivery element when the elongate medication-delivery element has the compressed shape.

For some applications, the pill has a length of between 5 and 30 mm before the coating dissolves.

For some applications, the compressed shape is selected from the group of shapes consisting of: a serpentine shape, a sinusoidal shape, and a zigzag shape.

For some applications, the compressed shape is helical.

For some applications, the elongate medication-delivery element is rolled when in the compressed shape.

For some applications, the elongate medication-delivery element includes one or more anchors, which are configured to anchor the elongate medication-delivery element to the intestinal wall. For some applications, the anchors are dissolvable. For some applications, the anchors are shaped as claws.

For some applications, the pill includes a shell, which includes the coating.

For some applications, the core, when disposed within the coating, is directly coated with the coating.

For some applications, the elongate medication-delivery element is biodegradable.

For some applications, the elongate medication-delivery element is configured to break apart in the small intestine.

For some applications, the medication includes a liquid that is absorbed in the elongate medication-delivery element.

For some applications, the elongate medication-delivery element includes one or more threads, which are configured to intertwine with villi of the small intestine. For some applications, each of at least 90% of the threads has a diameter of between 20 and 50 microns. For some applications, each of at least 90% of the threads has a length of between 1 and 10 cm. For some applications, each of at least 90% of the threads has a length of between 10 and 50 cm. For some applications, the threads are biodegradable.

For some applications, the medication includes a powder.

For some applications, the coating includes a gelatin coating configured to constrain the elongate medication-delivery element from expanding before the gelatin coating dissolves.

For some applications, the pill further includes a chemical enhancer configured to enhance delivery of the medication to the subject.

For some applications, the chemical enhancer includes lipophilic molecules configured to enhance diffusion of the medication through an epithelial layer of the intestinal wall of the subject.

For some applications, the coating is pH-sensitive, and is configured to dissolve within 10 minutes only within a range of pH values, which range has a low end of between 6.5 and 8.5.

For any of the previous applications, at least 50% of a length of the elongate medication-delivery element, measured along the longitudinal axis of the elongate medication-delivery element, may be shaped as a helix when the elongate medication-delivery element has the expanded shape and is unconstrained. For some applications, at least 75% of the length is shaped as the helix when the elongate medication-delivery element has the expanded shape and is unconstrained. For some applications, 100% of the length is shaped as the helix when the elongate medication-delivery element has the expanded shape and is unconstrained.

For some applications, the helix has at least 0.75 helix turns when the elongate medication-delivery element has the expanded shape and is unconstrained. For some applications, the helix has at least one helix turn when the elongate medication-delivery element has the expanded shape and is unconstrained. For some applications, the helix has at least two helix turns when the elongate medication-delivery element has the expanded shape and is unconstrained. For some applications, the helix has no more than three helix turns when the elongate medication-delivery element has the expanded shape and is unconstrained.

For some applications, when the elongate medication-delivery element has the expanded shape and is unconstrained, the helix radially surrounds a cylindrical space having a diameter perpendicular to a longitudinal axis of the cylindrical space of between 3 and 7 cm.

For some applications, the helix is a circular helix when the elongate medication-delivery element has the expanded shape and is unconstrained. For some applications, the helix has an outer diameter of between 4 and 7 cm when the elongate medication-delivery element has the expanded shape and is unconstrained.

For some applications, when the elongate medication-delivery element has the expanded shape and is unconstrained:

the medication is disposed on the outer surface of the elongate medication-delivery element around a circumferential portion of the elongate medication-delivery element at least along a longitudinal segment of the elongate medication-delivery element, which circumferential portion subtends an angle of between 45 and 135 degrees, and which longitudinal segment has a length of at least 1 cm, measured along the longitudinal axis of the elongate medication-delivery element, and the circumferential portion, at all locations along the longitudinal segment, includes a radially-outermost surface of the helix.

For some applications, the circumferential portion subtends an angle of between 75 and 105 degrees.

For any of the previous applications, the elongate medication-delivery element may have an average compressed cross-sectional area perpendicular to the longitudinal axis of the elongate medication-delivery element when the elongate medication-delivery element has the compressed shape, and an average expanded cross-sectional area perpendicular to the longitudinal axis of the elongate medication-delivery element when the elongate medication-delivery element has the expanded shape and is unconstrained, the average expanded cross-sectional area greater than the average compressed cross-sectional area. For some applications, the average expanded cross-sectional area is at least 300% of the average compressed cross-sectional area. For some applications, the elongate medication-delivery element is configured to transition from the average compressed cross-sectional area to the average expanded cross-sectional area by absorbing a fluid. For some applications, the elongate medication-delivery element includes a material that is configured to generate a gas when exposed to the fluid.

For any of the previous applications, the medication may be disposed on the outer surface of the elongate medication-delivery element. For some applications, when the elongate medication-delivery element has the expanded shape and is unconstrained, the outer surface of the elongate medication-delivery element has a surface area, and the medication is disposed on less than 50% of the surface area. For some applications, when the elongate medication-delivery element has the expanded shape and is unconstrained, the medication is disposed on the outer surface around a circumferential portion of the elongate medication-delivery element at least along a longitudinal segment of the elongate medication-delivery element, which circumferential portion subtends an angle of between 45 and 135 degrees, and which longitudinal segment has a length of at least 5 mm, measured along the longitudinal axis. For some applications, the circumferential portion subtends an angle of between 75 and 105 degrees. For some applications, a circumferential orientation of the circumferential portion varies along the longitudinal segment. For some applications, the pill further includes a mucoadhesive coated on a portion of the outer surface of the elongate medication-delivery element at which the medication is disposed.

For some applications, the medication is disposed along at least 75% of a length of the elongate medication-delivery element, measured along the longitudinal axis of the elongate medication-delivery element, when the elongate medication-delivery element has the expanded shape and is unconstrained.

For some applications, the medication is disposed on the outer surface of the elongate medication-delivery element so as to define a plurality of protrusions, each of which has a length of between 50 and 300 microns. For some applications, a greatest radius of each of the protrusions is between 20 and 100 microns.

For some applications, the elongate medication-delivery element is configured such that when the elongate medication-delivery element has the expanded shape, the medication disposed on the outer surface contacts the intestinal wall providing 360 degrees of contact of the medication with the intestinal wall.

For some applications, the elongate medication-delivery element is configured such that when the elongate medication-delivery element has the expanded shape and is disposed in a circular cylinder having an inner diameter of 2.5 cm, the medication disposed on the outer surface has 360 degrees of contact with an inner surface of the cylinder.

There is also provided, in accordance with an application of the present invention, a method including:

receiving, by a subject, an ingestible pill, which includes (i) a coating configured to dissolve in a small intestine of the subject, and (ii) a core, which includes an elongate medication-delivery element having an outer surface and a longitudinal axis, wherein the elongate medication-delivery element (a) has a compressed shape when disposed within the coating, (b) is configured to assume, after the coating dissolves, an expanded shape of a three-dimensional space curve, and (c) includes a medication; and swallowing the ingestible pill by the subject, so that the coating dissolves in the small intestine, the elongate medication-delivery element assumes the expanded shape, and the medication contacts an intestinal wall of the subject when the elongate medication-delivery element has the expanded shape.

There is further provided, in accordance with an application of the present invention, apparatus including an ingestible pill, which includes:

a coating configured to dissolve in a small intestine of a subject; and a core, which includes a sponge, which (a) has a compressed shape and compressed volume when disposed within the coating, (b) is configured to assume, after the coating dissolves, an expanded shape and an expanded volume, the expanded volume at least 3 times the compressed volume, and (c) includes a medication and a mucoadhesive.

For some applications, the mucoadhesive is disposed on a portion of an outer surface of the sponge, which outer surface is configured such that the mucoadhesive contacts an intestinal wall of the subject when the sponge has the expanded shape.

For some applications, the pill includes a shell, which includes the coating.

For some applications, the core, when disposed within the coating, is directly coated with the coating.

For some applications, the sponge is biodegradable.

For some applications, the sponge is configured to break apart.

For some applications, the mucoadhesive is mixed with the medication.

For some applications, the medication includes a liquid that is absorbed in the sponge.

For some applications, the sponge includes one or more threads, which are configured to intertwine with villi of the small intestine. For some applications, each of at least 90% of the threads has a diameter of between 20 and 50 microns. For some applications, each of at least 90% of the threads has a length of between 1 and 10 cm. For some applications, each of at least 90% of the threads has a length of between 10 and 50 cm. For some applications, the threads are biodegradable.

For some applications, the coating includes a gelatin coating configured to constrain the sponge from expanding before the gelatin coating dissolves.

For some applications, the pill further includes a chemical enhancer configured to enhance delivery of the medication to the subject.

For some applications, the chemical enhancer includes lipophilic molecules configured to enhance diffusion of the medication through an epithelial layer of the intestinal wall of the subject.

For some applications, the coating is pH-sensitive, and is configured to dissolve within 10 minutes only within a range of pH values, which range has a low end of between 6.5 and 8.5.

For any of the previous applications, the medication may be disposed on at least a portion of an outer surface of the sponge, which outer surface is configured such that the medication contacts an intestinal wall of the subject when the sponge has the expanded shape. For some applications, the mucoadhesive is disposed on at least a portion of the outer surface of the sponge. For some applications, when the sponge has the expanded shape and is unconstrained, the outer surface of the sponge has a surface area, and the medication is disposed on less than 50% of the surface area. For some applications, when the sponge has the expanded shape and is unconstrained, the mucoadhesive is disposed on less than 50% of the surface area. For some applications, when the sponge has the expanded shape and is unconstrained, more of the mucoadhesive is disposed on one side of the sponge than on another side of the sponge.

For some applications, the medication is disposed on the outer surface of the sponge so as to define a plurality of protrusions, each of which has a length of between 50 and 300 microns. For some applications, a greatest radius of each of the protrusions is between 20 and 100 microns.

For some applications, the medication includes a powder.

There is still further provided, in accordance with an application of the present invention, a method including:

receiving, by a subject, an ingestible pill, which includes (i) a coating configured to dissolve in a small intestine of the subject, and (ii) a core, which includes a sponge, which (a) has a compressed shape and compressed volume when disposed within the coating, (b) is configured to assume, after the coating dissolves, an expanded shape and an expanded volume, the expanded volume at least 3 times the compressed volume, and (c) includes a medication and a mucoadhesive; and swallowing the ingestible pill by the subject, so that the coating dissolves in the small intestine, and sponge assumes the expanded shape.

There is additionally provided, in accordance with an application of the present invention, apparatus including an ingestible pill, which includes:

a coating configured to dissolve in a small intestine of a subject; and a core, which includes a medication-delivery ring, which (a) has a compressed shape when disposed within the coating, (b) is configured to assume, after the coating dissolves, an expanded shape, and (c) includes a medication, wherein, when the medication-delivery ring is unconstrained in the expanded shape, the medication-delivery ring has (a) an outer perimeter of between 6 and 30 cm, and (b) a thickness, measured in a direction perpendicular to a plane defined by the outer perimeter, of less than 0.5 cm, and wherein the medication-delivery ring is configured such that the medication contacts an intestinal wall of the subject when the medication-delivery ring has the expanded shape.

For some applications, the medication-delivery ring includes a sponge.

For some applications, the medication-delivery ring is biodegradable in the small intestine.

For some applications, the thickness is less than 0.3 cm when the medication-delivery ring is unconstrained in the expanded shape.

For some applications, an average width of the medication-delivery ring, measured between the outer perimeter of the medication-delivery ring and an inner perimeter of the medication-delivery ring, equals at least 3 times the thickness, when the medication-delivery ring is unconstrained in the expanded shape.

For some applications, an average width of the medication-delivery ring, measured between the outer perimeter of the medication-delivery ring and an inner perimeter of the medication-delivery ring, equals at least 3 mm, when the medication-delivery ring is unconstrained in the expanded shape.

For some applications, the medication-delivery ring is shaped so as to define first and second surfaces on opposite sides of the medication-delivery ring, and the medication at least partially coats the first surface. For some applications, the pill further includes a mucoadhesive, which at least partially coats the first surface.

For any of the previous applications, the medication-delivery ring may be inflatable and may be shaped so as to define at least one internal chamber, the medication-delivery ring may be uninflated when in the compressed shape when disposed within the coating, and the medication-delivery ring may be configured to assume the expanded shape upon inflation.

For some applications:

the medication-delivery ring further comprises sodium bicarbonate and a substance selected from the group consisting of: an acid and water, when in the compressed shape, the medication-delivery ring is folded into at least first and second segments, the substance is disposed in the medication-delivery ring in the first segment, and the sodium bicarbonate is disposed in the medication-delivery ring in the second segment.

For some applications, the medication-delivery ring includes radial ribs, which are configured to prevent over-inflation.

For any of the previous applications, the medication-delivery ring may include an elastomer. For some applications, the elastomer includes silicone.

There is yet additionally provided, in accordance with an application of the present invention, a method including:

receiving, by a subject, an ingestible pill, which includes (i) a coating configured to dissolve in a small intestine of the subject, and (ii) a core, which includes a medication-delivery ring, which (a) has a compressed shape when disposed within the coating, (b) is configured to assume, after the coating dissolves, an expanded shape, and (c) includes a medication, wherein, when the medication-delivery ring is unconstrained in the expanded shape, the medication-delivery ring has (a) an outer perimeter of between 6 and 30 cm, and (b) a thickness, measured in a direction perpendicular to a plane defined by the outer perimeter, of less than 0.5 cm; and swallowing the ingestible pill by the subject, so that the coating dissolves in the small intestine, the medication-delivery ring assumes the expanded shape, and the medication contacts an intestinal wall of the subject when the medication-delivery ring has the expanded shape.

The present invention will be more fully understood from the following detailed description of embodiments thereof, taken together with the drawings, in which:

BRIEF DESCRIPTION OF THE DRAWINGS

FIGS. 3A-B are schematic illustrations of another configuration of the medication-delivery element of the ingestible pill of FIGS. 1A-F, in accordance with an application of the present invention;

FIG. 4 is a schematic illustration of yet another configuration of the medication-delivery element of the ingestible pill of FIGS. 1A-F, in accordance with an application of the present invention;

FIGS. 7A-C are schematic illustrations of still another configuration of the medication-delivery element of the ingestible pill of FIGS. 1A-F, in accordance with an application of the present invention;

FIGS. 10A-C are schematic illustrations of another ingestible pill, for ingestion by a subject, in accordance with an application of the present invention;

FIG. 11 is a schematic illustration of a configuration of an elongate medication-delivery element of the ingestible pill of FIGS. 10A-C, in accordance with an application of the present invention;

DETAILED DESCRIPTION OF EMBODIMENTS

Figure 1A:
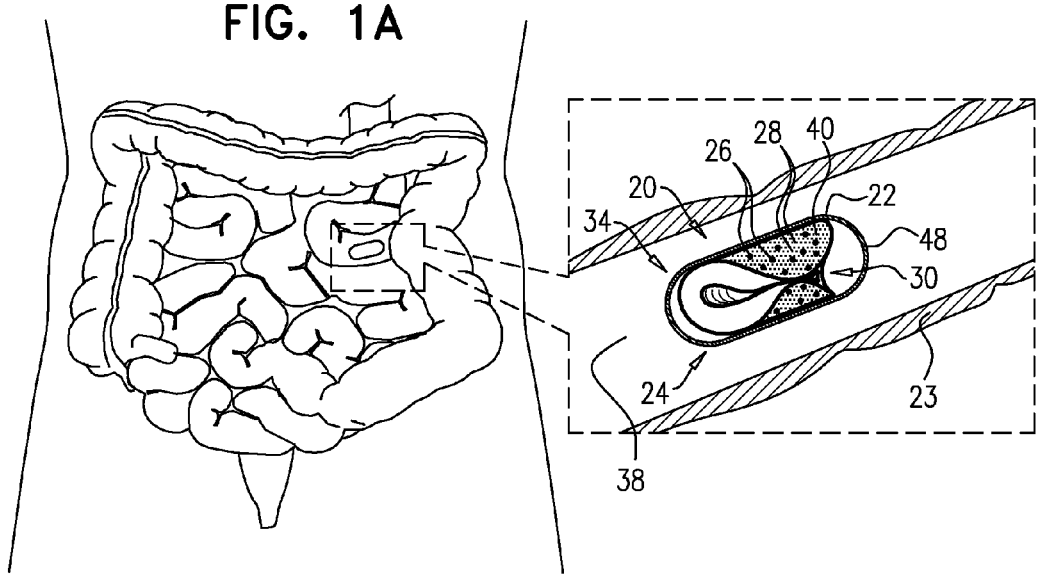
FIGS. 1A-F are schematic illustrations of an ingestible pill, for ingestion by a subject, in accordance with an application of the present invention.

FIGS. 1A-F are schematic illustrations of an ingestible pill 20, for ingestion by a subject, in accordance with an application of the present invention. Ingestible pill 20 comprises a coating 22, a core 24, a medication 26, and, optionally, a mucoadhesive 28. Coating 22 is configured to dissolve in a small intestine 23 (e.g., a duodenum, jejunum, and/or ileum) of the subject. For example, coating 22 may be enteric, e.g., pH-sensitive, and may be configured to dissolve within 10 minutes (e.g., within 5 minutes) within a range of pH values, which range has a low end of between 6.5 and 8.5 (and, optionally, a high end of between 7.5 and 14, such as between 7.5 and 9.5). For example, coating 22 may comprise gelatin. For some applications, as shown in FIG. 1A, pill 20 comprises a shell 48, which comprises coating 22. Alternatively, for some applications, core 24 is directly coated with coating 22 (configuration not shown). Typically, pill 20 has a length of at least 5 mm, no more than 30 mm, and/or between 5 and 30 mm before the coating dissolves.

Core 24 comprises a medication-delivery element 30, which (a) has a compressed shape 34 when disposed within coating 22, as shown in FIG. 1A, and (b) is configured to assume, after coating 22 dissolves, an expanded shape 36. Optionally, core 24 comprises a plurality of medication-delivery elements 30.

Figure 1B:
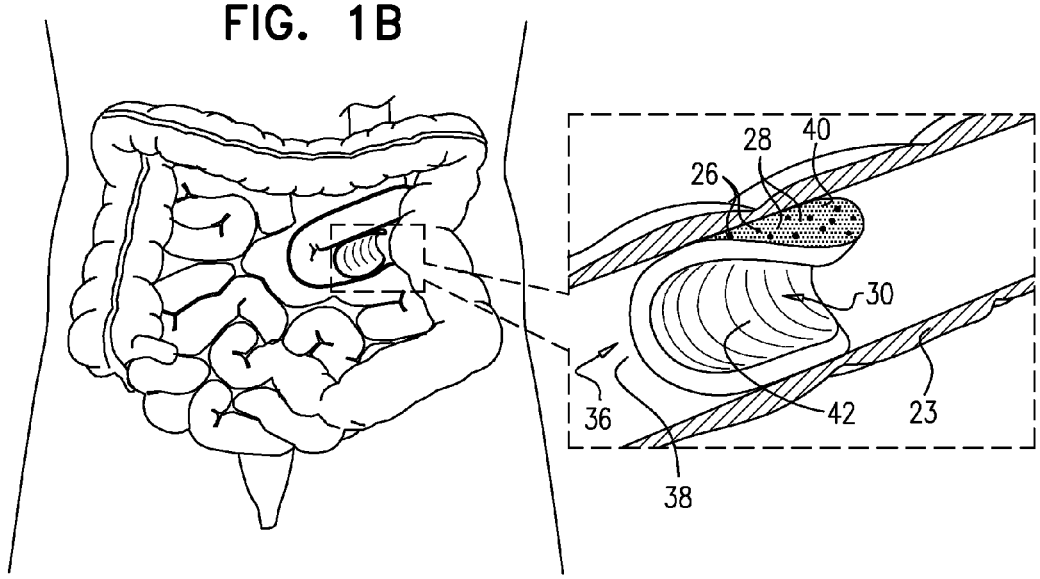
Figure 1C:
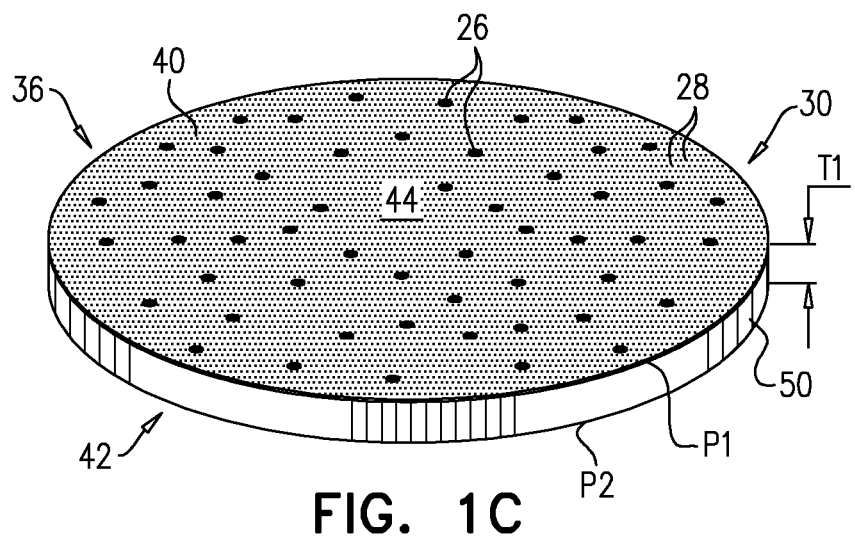
Figure 1D:
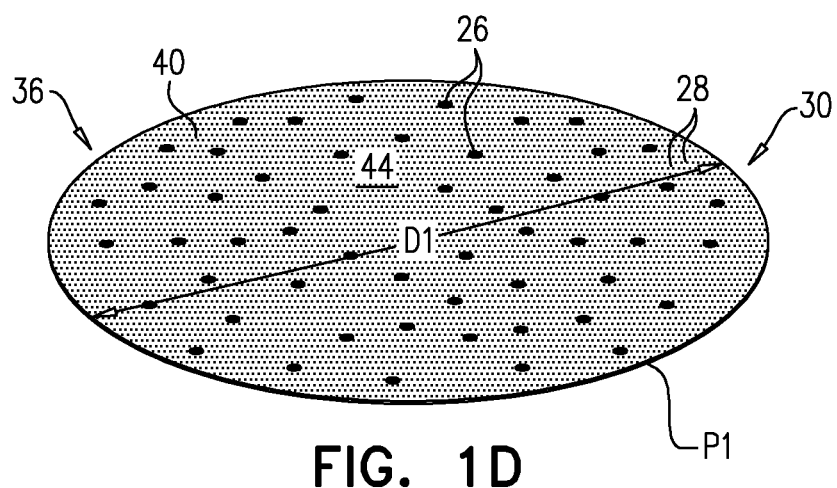
Figure 1E:
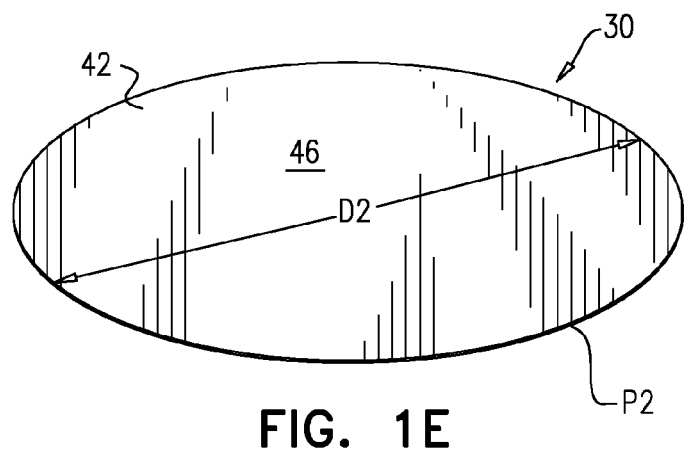

FIG. 1B shows medication-delivery element 30 in expanded shape 36, constrained by a wall 38 of small intestine 23, while FIGS. 1C-F show medication-delivery element 30 unconstrained in expanded shape 36. FIG. 1C is an isometric view of medication-delivery element 30, and FIGS. 1D and 1E are top-views of two sides of medication-delivery element 30, as described immediately below.

When unconstrained in expanded shape 36, medication-delivery element 30:
- is shaped so as to define first and second surfaces 40 and 42 on opposite sides of medication-delivery element 30; and
- has an average thickness T1 of an edge 50 between first and second surfaces 40 and 42 of less than 6 mm, such as less than 4 mm, and/or at least 0.5 mm, such as at least 1 mm, e.g., between 0.5 and 6 mm, such as between 1 and 6 mm, such as between 1 and 4 mm.

First and second surfaces 40 and 42 have respective outer perimeters P1 and P2, which surround respective spaces 44 and 46 of respective surfaces 40 and 42. Spaces 44 and 46 typically have respective greatest dimensions D1 and D2 (e.g., respective diameters for configurations in which medication-delivery element 30 is circular) equal to at least 55% of the circumference of small intestine 23, no more than 90% (e.g., no more than 80%) of the circumference, and/or between 55% and 90% (e.g., between 55% and 80%) of the circumference, such that when medication-delivery element 30 is in expanded shape 36, it generally presses outward against the intestinal wall. The circumference of the small intestine is typically between 6 cm (e.g., in children and small adults) and 9 cm (e.g., in average-size adults). Thus, each of greatest dimensions D1 and D2 (e.g., each of respective diameters for configurations in which medication-delivery element 30 is circular) is typically between 3.3 and 5.4 cm for use in children and smaller adults, and between 5 and 8 cm for use in average-size adults, or, overall for the human population, at least 3.3 cm, no more than 8 cm, and/or between 3.3 and 8 cm. Alternatively, for some applications, each of greatest dimensions D1 and D2 (e.g., respective diameters for configurations in which medication-delivery element 30 is circular) is at least 2 cm (e.g., at least 3 cm, such as at least 4 cm), no more than 10 cm (e.g., no more than 7 cm), and/or between 2 and 10 cm (e.g., between 2 and 7 cm, such as between 3 and 7 cm, or between 4 and 7 cm). For some applications, the outer perimeter P1 (e.g., the outer circumference for configurations in which the ring is circular) of medication-delivery element 30 is at least 6 cm, no more than 30 cm, and/or between 6 and 30 cm.

Each of spaces 44 and 46 has an area equal to at least 50% of the square of the greatest dimension of the space, such as at least 75% of the square of the greatest dimension.

Each of medication 26 and mucoadhesive 28 at least partially coats first surface 40. For example, medication 26 and/or mucoadhesive 28 may be sprayed or printed on first surface 40 using techniques known in the art. For some applications, mucoadhesive 28 is mixed with medication 26, as symbolically shown in FIGS. 1A-E, 2, 3A-B, 4, 5A-C, 6A-F, 7A-C, and 8. Alternatively, for some applications, mucoadhesive 28 is arranged as dots on first surface 40. Further alternatively, medication 26 and mucoadhesive 28 are arranged generally separately on first surface 40, such as described, for example, with reference to FIG. 1F. Mucoadhesive 28 transiently adheres first surface 40 in position against the intestinal wall during delivery of medication 26 through the intestinal wall. For example, mucoadhesive 28 may include an adhesive agent described in U.S. Pat. No. 6,235,313 to Mathiowitz et al., or in an article by Tao et al., Tao et al., entitled, "Gastrointestinal patch systems for oral drug delivery," Drug Discovery Today, Vol. 10(13), July 2005, both of which references are incorporated herein by reference.

For some applications, a non-adhesive material, such as silicone, coats second surface 42, to reduce the likelihood of prolonged contact of second surface 42 with wall 38 of small intestine 23. For some applications, medication 26 comprises a powder, a gel, or a liquid (which may be absorbed in medication-delivery element 30, but available to first surface 40).

For some applications, at least 67%, such as at least 90% (e.g., at least 98%, such as 100%) of medication 26, by weight, is disposed on first surface 40. Alternatively or additionally, for some applications, less than 10% (e.g., less than 2%, such as none) of medication 26, by weight, is disposed on second surface 42. Alternatively or additionally, for some applications, at least 67%, such as at least 90% (e.g., at least 98%, such as 100%) of mucoadhesive 28, by weight, is disposed on the first surface. Alternatively or additionally, for some applications, less than 10% (e.g., less than 2%, such as none) of mucoadhesive 28, by weight, is disposed on the second surface. For some applications, second surface 42 is generally impermeable to medication 26.

Medication-delivery element 30 expands, such as by stretching, unfolding, and/or unrolling, in response to no longer being constrained by coating 22, and/or in response to contact of core 24 with fluid in the small intestine. Once expanded, first surface 40 establishes good (complete or nearly complete) contact with wall 38 of small intestine 23, as shown in FIG. 1B. Factors contributing to this good contact include: (a) the shape and dimensions of medication-delivery element 30, which prevent other, lower-contact-level orientations of the element in the lumen of the small intestine, and (b) the disposition of mucoadhesive 28 on first surface 40, which holds expanded first surface 40 in position during delivery of medication 26, in applications in which the mucoadhesive is provided. Because of this good contact, medication 26 disposed on first surface 40 typically makes contact with intestinal wall 38, enhancing diffusion of the medication through the wall. This good contact, typically in combination with the high concentration of medication 26 on first surface 40, results in delivery of a high quantity of medication 26 through intestinal wall 38.

Alternatively, if medication 26 is only disposed on a smaller portion of first surface 40, such as described below with reference to FIG. 1F, the contact area is correspondingly reduced. Alternatively or additionally, the delivery of the medication through the intestinal wall is enhanced by incorporating a chemical enhancer in the ingestible pill, e.g., by incorporating the chemical enhancer into medication 26. For example, lipophilic molecules may be incorporated into the ingestible pill, which enhance diffusion of the medication across the epithelial layer of the subject's gastrointestinal tract.

Following delivery of medication 26, core 24, including medication-delivery element 30, is passed from the body. For some applications, core 24, including medication-delivery element 30, comprises a biodegradable substance, which biodegrades to facilitate its separation from the wall of the small intestine following delivery of the medication, typically within 1 to 12 hours after the coating dissolves. Alternatively or additionally, core 24 comprises a polymer that absorbs water, expands in the small intestine, and is subsequently broken down by bacteria and/or by the pH found in the colon. In this manner, medication-delivery element 30, which had been substantially enlarged to facilitate drug delivery, decreases in size or otherwise is enabled to separate from the wall of the small intestine or to pass easily from the subject's body. Alternatively, core 24, including medication-delivery element 30, is removed from the body by being passed from the body, without a reduction in size. Thus, as appropriate, the core may be configured to (a) decrease in size in the small intestine, following medication delivery, (b) decrease in size in the colon, or (c) not decrease in size following medication delivery.

For some applications, medication-delivery element 30 comprises a biodegradable polymer (e.g., PGA) mixed with a flexible material, such as silicone. For example, the flexible material may be shaped as small elements, such as fibers or other shapes. Biodegradable polymers are typically relatively inflexible. Mixing the flexible material with the polymer increases the flexibility, while still retaining some of the favorable properties of the polymer, such as its biodegradability. The flexible material is mixed with the polymer before the polymer is molded into the shape of medication-delivery element 30. Typically, each of the small elements has a diameter of at least 0.1 mm, no more than 0.5 mm, and/or between 0.1 mm and 0.5 mm, and/or a length of at least 2 mm, no more than 10 mm, and/or between 2 and 10 mm. Typically, medication-delivery element 30 comprises at least 10, no more than 10,000, and/or between 10 and 10,000 of these small elements.

For some applications, medication-delivery element 30 is rolled when in compressed shape 34 within coating 22, such as shown in FIG. 1A.

For some applications, such as shown in FIG. 1A, at least 75% (e.g., at least 90%, such as 100%) of first surface 40 faces at least partially radially outwardly, when medication-delivery element 30 has compressed shape 34 when disposed within coating 22. For some applications, during manufacture, medication-delivery element 30 is first rolled such that first surface faces at least partially radially outward, and then compressed.

For some applications, as shown, first and second surfaces 40 and 42 are identical in size and shape. For other applications, first and second surfaces having slightly different sizes and/or shapes (configuration not shown).

For some applications, first and second surfaces 40 and 42 are circular, and greatest dimensions D1 and D2 are respective diameters of first and the second surfaces 40 and 42. For some applications, first and second surfaces 40 and 42 are rectangular, and greatest dimensions D1 and D2 are respective diagonals of first and second surfaces 40 and 42. For some applications, first and second surfaces 40 and 42 are polygonal. For some applications, first and second surfaces 40 and 42 are elliptical.

For some applications, as shown in FIGS. 1C-E, medication-delivery element 30, when unconstrained in expanded shape 36, is generally flat. Alternatively, medication-delivery element 30, when unconstrained in expanded shape 36, is curved out of plane (configuration not shown); for example, medication-delivery element 30 may have a radius of curvature of at least 1.25 cm, no more than 3 cm, and/or between 1.25 and 3 cm.

Figure 1F:
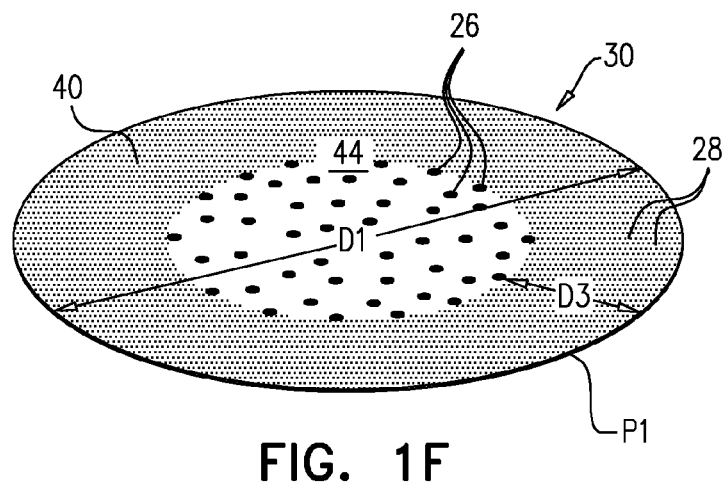

For some applications, such as shown in FIG. 1F, mucoadhesive 28 is generally disposed near perimeter P1 of first surface 40, and medication 26 is generally disposed in a central portion of first surface 40 away from perimeter P1. This arrangement may provide good adhesion of the perimeter of the first surface, and thus the entire first surface, with the wall of the small intestine, which holds the first surface in position during delivery of medication 26 through the wall of the small intestine. For example, 90% of mucoadhesive 28 may disposed within a distance D3 of perimeter P1, which distance D3 equals 25% of greatest dimension D1 of first surface 40, or 15% of greatest dimension D1 of first surface 40. Alternatively or additionally, for example, 90% of medication 26 may be disposed more than distance D3 from perimeter P1, which distance D3 equals 25% of greatest dimension D1 of first surface 40, or 15% of greatest dimension D1 of first surface. Alternatively or additionally, for example, mucoadhesive 28 may be disposed on an outer 50%-75% of first surface 40, and medication 26 may be disposed in a central 25%-50% of first surface 40. For some applications, the techniques described with reference to FIG. 1F are used in combination with the configurations of medication-delivery element 30 described hereinbelow with reference to FIGS. 5A-C, 6A-F, 7A-C, and 8.

For some applications, medication-delivery element 30 comprises an elastomer, such as silicone.

Alternatively, for some applications, medication-delivery element 30 comprises a sponge, i.e., a soft, light porous substance. The use of a sponge may avoid putting any rigid materials against the villi and/or folds of the wall of the small intestine. For some applications, the sponge comprises gelatin and/or polyurethane. For some applications, the sponge is biodegradable in whole or in part (typically within 1 to 12 hours after the coating dissolves), while for other applications the sponge is not biodegradable. For some applications, medication 26 comprises a liquid that is absorbed in the sponge, but is available to the outer surface of the sponge. For example, medication 26 may be in oily suspension. Alternatively or additionally, for some applications, medication 26 is coated (e.g., printed) on an outer surface of the sponge, in which case medication may comprise a dry material, such as a powder.

Figure 2:
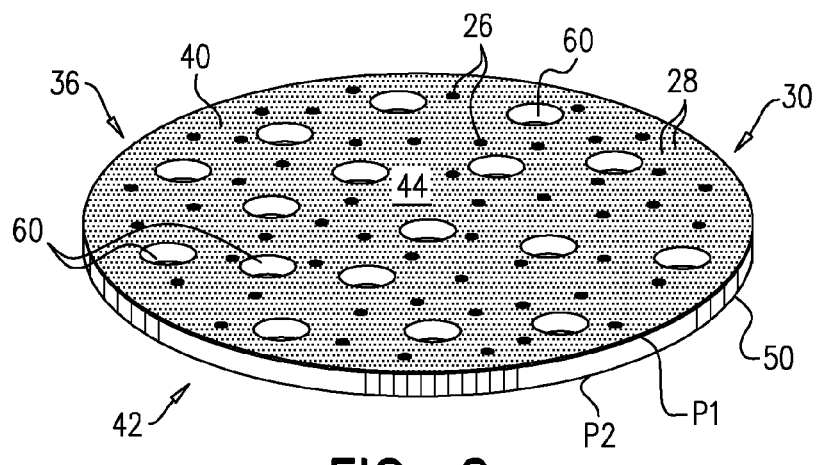
FIG. 2 is a schematic illustration of a configuration of a medication-delivery element of the ingestible pill of FIGS. 1A-F, in accordance with an application of the present invention.

Reference is now made to FIG. 2, which is a schematic illustration of a configuration of medication-delivery element 30, in accordance with an application of the present invention. In this configuration, medication-delivery element 30, when unconstrained in expanded shape 36 (as shown), is shaped so as to define a plurality of openings 60 therethrough. These openings may allow for high compression of medication-delivery element 30 when in compressed shape 34 when disposed within coating 22, while still providing good contact with the intestinal wall of the portion of first surface 40 that is coated with medication 26. Providing the openings thus does not necessarily decrease the total drug-coated surface area that contacts the intestinal wall.

For some applications, when medication-delivery element 30 is unconstrained in expanded shape 36, such as shown in FIG. 2, an aggregate area of openings 60 equals at least 10% (e.g., at least 30%) of the area of space 44 surrounded by outer perimeter P1 of first surface 40, no more than 60% (e.g., no more than 50%) of the area of the space, and/or between 10% and 60% of the area of the space, e.g., between 30% and 50% of the area of the space. Alternatively or additionally, an average area of openings 60 equals at least 0.5% (e.g., at least 1%), no more than 10% (e.g., no more than 5%), and/or between 0.5% and 10%, such as between 1% and 5%, of the area of the space. Alternatively or additionally, for some applications, an average area of openings 60 equals at least 1 mm2, no more than 50 mm2 (e.g., no more than 12 mm2), and/or between 1 and 50 mm, such as between 1 and 5 mm2, between 1 and 12 mm2, and/or between 12 and 50 mm2. For some applications, medication-delivery element 30 is shaped so as to define at least 4 openings (e.g., at least 6 openings), no more than 100 openings (e.g., no more than 20 openings), and/or between 4 and 100 openings, such as between 6 and 20 openings.

Reference is now made to FIGS. 3A-B, which are schematic illustrations of another configuration of medication-delivery element 30, in accordance with an application of the present invention. FIG. 3A shows medication-delivery element 30 unconstrained in expanded shape 36. FIG. 3B shows medication-delivery element 30 in expanded shape 36, constrained by wall 38 of small intestine.

In this configuration, medication-delivery element 30, when unconstrained in expanded shape 36 (as shown in FIG. 3A), is shaped so as to define an opening 70 therethrough. This opening may allow for high compression of medication-delivery element 30 when in compressed shape 34 when disposed within coating 22, while still providing good contact of first surface 40 with the wall of the small intestine for drug delivery when medication-delivery element 30 is in expanded shape 36.

For some applications, when medication-delivery element 30 is unconstrained in expanded shape 36, such as shown in FIG. 3A, an area of opening 70 equals at least 25%, no more than 90%, and/or between 25% and 90% of the area of space 44 surrounded by outer perimeter P1 of first surface 40, such as at least 50%, no more than 85%, and/or between 50% and 85% of the area of the space. Alternatively or additionally, for some applications, the area of opening 70 is at least 2.5 cm2, no more than 70 cm2, and/or between 2.5 cm2 and 70 cm2. For some applications, medication-delivery element 30 is circular, and greatest dimension D1 is a diameter of medication-delivery element 30, when medication-delivery element 30 is unconstrained in expanded shape 36.

For some applications, such as shown in FIGS. 3A-B, medication-delivery element 30 is shaped so as to define only a single opening 70, and no other openings.

Reference is now made to FIG. 4, which is a schematic illustration of yet another configuration of medication-delivery element 30, in accordance with an application of the present invention. In this configuration, medication-delivery element 30, when unconstrained in expanded shape 36 (as shown), is shaped so as to define a plurality of openings therethrough, including a large central opening 70 and a plurality of smaller second openings 60 arranged around central opening 70, between central opening 70 and outer perimeter P1.

For some applications, when medication-delivery element 30 is unconstrained in expanded shape 36, such as shown in FIG. 4, an area of opening 70 equals at least 25%, no more than 90%, and/or between 25% and 90% of the area of space 44 surrounded by outer perimeter P1 of first surface 40, such as at least 50%, no more than 85%, and/or between 50% and 85% of the area of the space. Alternatively or additionally, for some applications, the area of opening 70 is at least 2.5 cm2, no more than 70 cm2, and/or between 2.5 cm2 and 70 cm2. Further alternatively or additionally, for some applications, when medication-delivery element 30 is unconstrained in expanded shape 36, an average area of smaller second openings 60 equals at least 1%, no more than 10%, and/or between 1% and 10% of the area of space 44, such as at least 2%, no more than 5%, and/or between 2% and 5% of the area of the space.

Reference is made to both FIGS. 3A-B and 4. For some applications, as shown in FIGS. 3A-B and 4, medication-delivery element 30 is shaped as a ring around opening 70, when medication-delivery element 30 is unconstrained in expanded shape 36. For these applications, medication-delivery element 30 may be considered to be shaped as an annulus, such as a thin annulus. For some applications, the outer perimeter P1 (e.g., the outer circumference for configurations in which the ring is circular) of the ring is at least 6 cm, no more than 30 cm, and/or between 6 and 30 cm.

Reference is still made to both FIGS. 3A-B and 4. For some applications, when medication-delivery element 30 is unconstrained in expanded shape 36, an average width W1 of medication-delivery element 30, measured between outer perimeter P1 of first surface 40 and opening 70, equals at least 3 times average thickness T1, no more than 8 times average thickness T1, and/or between 3 and 8 times average thickness T1, and/or equals at least 3 mm, no more than 12 mm, and/or between 3 and 12 mm. This relatively large width W1 facilitates proper alignment of medication-delivery element 30 around the wall of the small intestine, such as shown in FIG. 1B. In contrast, if shaped as a conventional o-ring, and with no further modifications, medication-delivery element 30 would not align properly against the wall of the small intestine. (When a conventional o-ring is squeezed on radially-opposite sides, e.g., at 12 o'clock and 6 o'clock, the o-ring may remain in plane or assume an unpredictable, arbitrary three-dimensional shape. In contrast, when the present configuration of medication-delivery element 30 is squeezed on radially-opposite sides by the intestinal wall, the relatively large width W1 causes the element to assume the desired shape shown in FIG. 1B, which properly aligns with the intestinal wall, as shown in FIG. 1B.)

Reference is still made to both FIGS. 3A-B and 4. For some applications, when medication-delivery element 30 is unconstrained in expanded shape 36, average thickness T1 is at least 0.5 mm, no more than 3 mm, and/or between 0.5 and 3 mm. For some applications, medication-delivery element 30 comprises an elastomer, such as silicone.

Figure 5A:
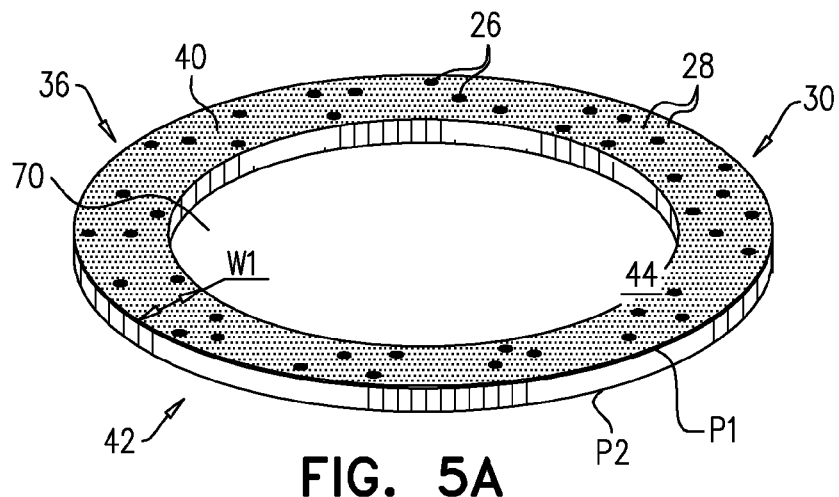
FIGS. 5A-C are schematic illustrations of a technique for compressing the medication-delivery element of the ingestible pill of FIGS. 1A-F, for disposal within a coating, in accordance with an application of the present invention.
Figure 5B:
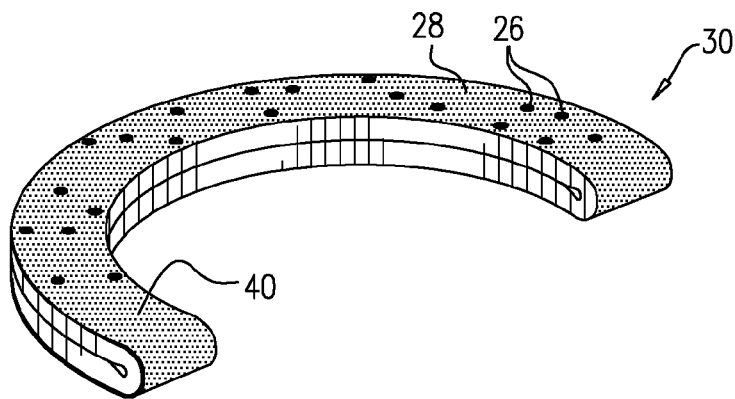
Figure 5C:
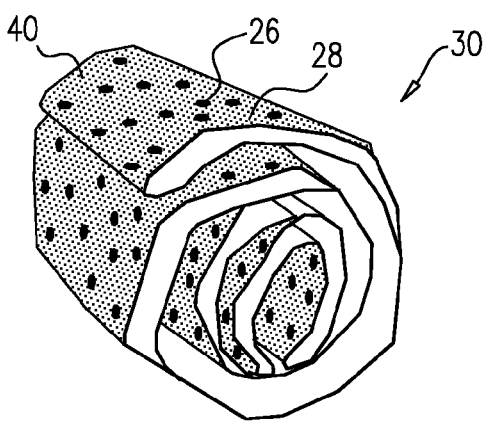

Reference is now made to FIGS. 5A-C, which are schematic illustrations of a technique for compressing medication-delivery element 30 for disposal within coating 22, in accordance with an application of the present invention. This techniques may be used for compressing the configuration of medication-delivery element 30 described with reference to FIGS. 3A-B (as shown in FIGS. 5A-C), or for compressing the configuration of medication-delivery element 30 described with reference to FIG. 4 (not shown in FIGS. 5A-C).

In this technique, medication-delivery element 30 is first folded onto itself as shown in FIG. 5B, and then rolled, as shown in FIG. 5C. As a result of this technique, when medication-delivery element 30 has the compressed shape, medication-delivery element 30 is in a folded configuration that is rolled (i.e., is in this folded and rolled state). Providing opening 70 allows this compact compressed shape to be achieved; without opening 70, medication-delivery element 30 would be larger if folded and rolled.

Reference is now made to FIGS. 6A-F, which are schematic illustrations of another technique for compressing medication-delivery element 30 for disposal within coating 22, in accordance with an application of the present invention. This techniques may be used for compressing the configuration of medication-delivery element 30 described with reference to FIGS. 3A-B (as shown in FIGS. 6A-F), or for compressing the configuration of medication-delivery element 30 described with reference to FIG. 4 (not shown in FIGS. 6A-F).

Figure 6A:
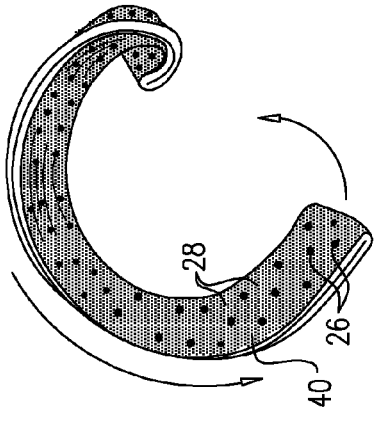
FIGS. 6A-F are schematic illustrations of another technique for compressing the medication-delivery element of the ingestible pill of FIGS. 1A-F, for disposal within a coating, in accordance with an application of the present invention.
Figure 6B:
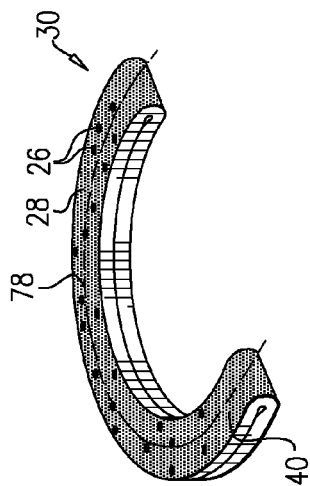
Figure 6C:
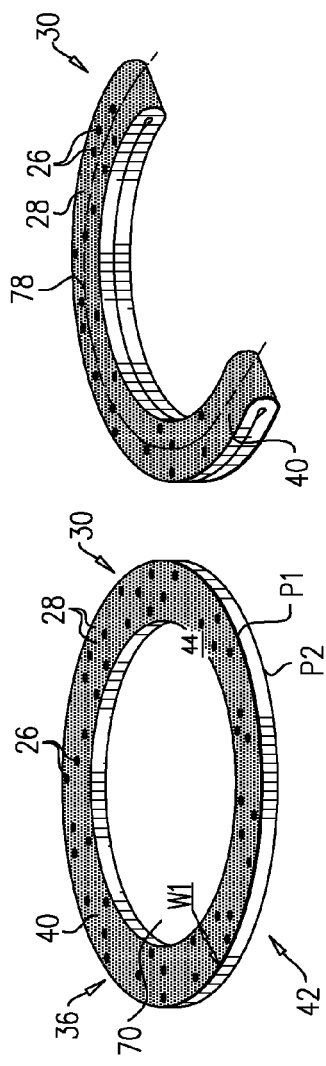
Figure 6D:
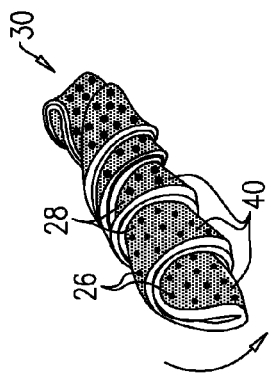
Figure 6E:
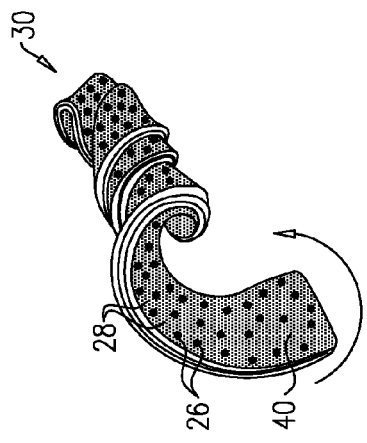
Figure 6F:
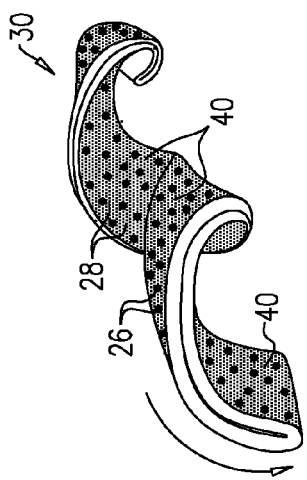

In this technique, medication-delivery element 30 is first folded onto itself as shown in FIG. 6B, and then twisted, typically generally about a semicircular longitudinal axis 78 of the folded shape, as shown in FIGS. 6C-F. As a result of this technique, when medication-delivery element 30 has the compressed shape, medication-delivery element 30 is in a folded configuration that is twisted (i.e., is in this folded and twisted state), as shown in FIG. 6F. Providing opening 70 allows this compact compressed shape to be achieved; without opening 70, medication-delivery element 30 would be larger if folded and twisted.

Figure 7C:
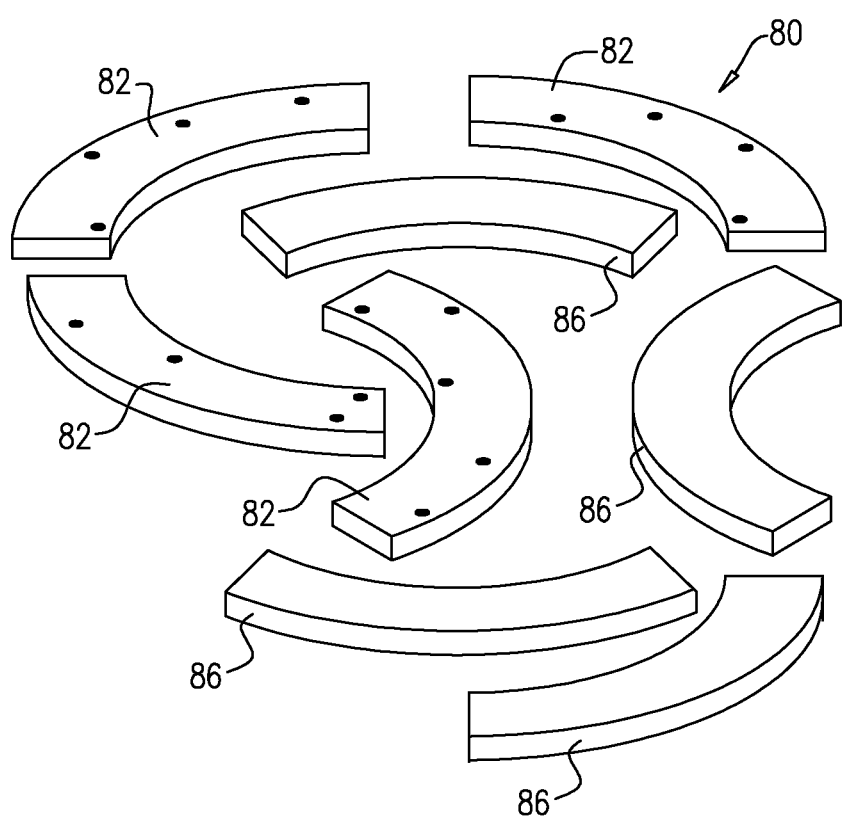

Reference is now made to FIGS. 7A-C, which are schematic illustrations of a still another configuration of medication-delivery element 30, in accordance with an application of the present invention. This configuration may be used in combination with the configuration of medication-delivery element 30 described with reference to FIGS. 3A-B (as shown in FIGS. 7A-C), or in combination with the configuration of medication-delivery element 30 described with reference to FIG. 4 (not shown in FIGS. 7A-C). In this configuration, medication-delivery element 30 is configured to break apart in the small intestine.

For some applications, in order to enable this breaking apart, medication-delivery element 30 comprises:
a first layer 80, which defines first surface 40, and which comprises a plurality of first pieces 82;
a second layer 84, which defines second surface 42 (in FIG. 7A, the underside of second layer 84, which cannot be seen), and which comprises a plurality of second pieces 86; and
a coupling material 88 that is biodegradable in the small intestine, and couples first and second layers 80 and 84 to one another; for example, the material may comprises a glue 89, which is spread between first and second layers 80 and 84, as shown in FIGS. 7A-B.

When first and second layers 80 and 84 are coupled to one another:
first pieces 82 are arranged such that they adjoin each other at respective first interfaces 90,
second pieces 86 are arranged such that they adjoin each other at respective second interfaces 92, and
first and second pieces 82 and 86 are arranged such that first interfaces 90 are offset from second interfaces 92.

For example, first and second pieces 82 and 86 may be arranged such that first interfaces 90 are rotationally offset from second interfaces 92, such as shown in FIGS. 7A-B. For some applications, first and second layers 80 and 84 comprise between two and ten first pieces 82 (such as between two and six first pieces 82) and between two and ten second pieces 86 (such as between two and six second pieces 86), respectively. For example, first and second layers 80 and 84 may comprise four first pieces 82 and four second pieces 86, respectively, as shown in FIGS. 7A-B; for example, first interfaces 90 may be disposed at 12 o'clock, 3 o'clock, 6 o'clock, and 9 o'clock, and second interfaces 92 may be disposed at half past 1 o'clock, half past 4 o'clock, half past 7 o'clock, and half past 10 o'clock, as shown in FIGS. 7A-B. Alternatively, for example, first and second layers 80 and 84 may comprise three first pieces 82 and three second pieces 86, respectively (configuration not shown); for example, first interfaces 90 may be disposed at 12 o'clock, 4 o'clock, and 8 o'clock, and second interfaces 92 may be disposed at 2 o'clock, 6 o'clock, and 10 o'clock.

After coupling material 88 (e.g., glue 89) biodegrades in the small intestine, first and second pieces 82 and 86 separate, as shown in FIG. 7C, and pass through the intestine.

For some applications, the techniques of FIGS. 7A-C are used in configurations in which medication-delivery element 30 is rolled when in compressed shape 34, such described hereinabove with reference to FIG. 1A or with reference to FIG. 5C, or twisted when in compressed shape 34, such described hereinabove with reference to FIG. 6F. If instead of using these techniques, only a single layer were provided with glue 89 between the interfaces between the pieces, medication-delivery element 30 would tend to fold or flex sharply at the interfaces, rather than roll or twist.

Figure 8:
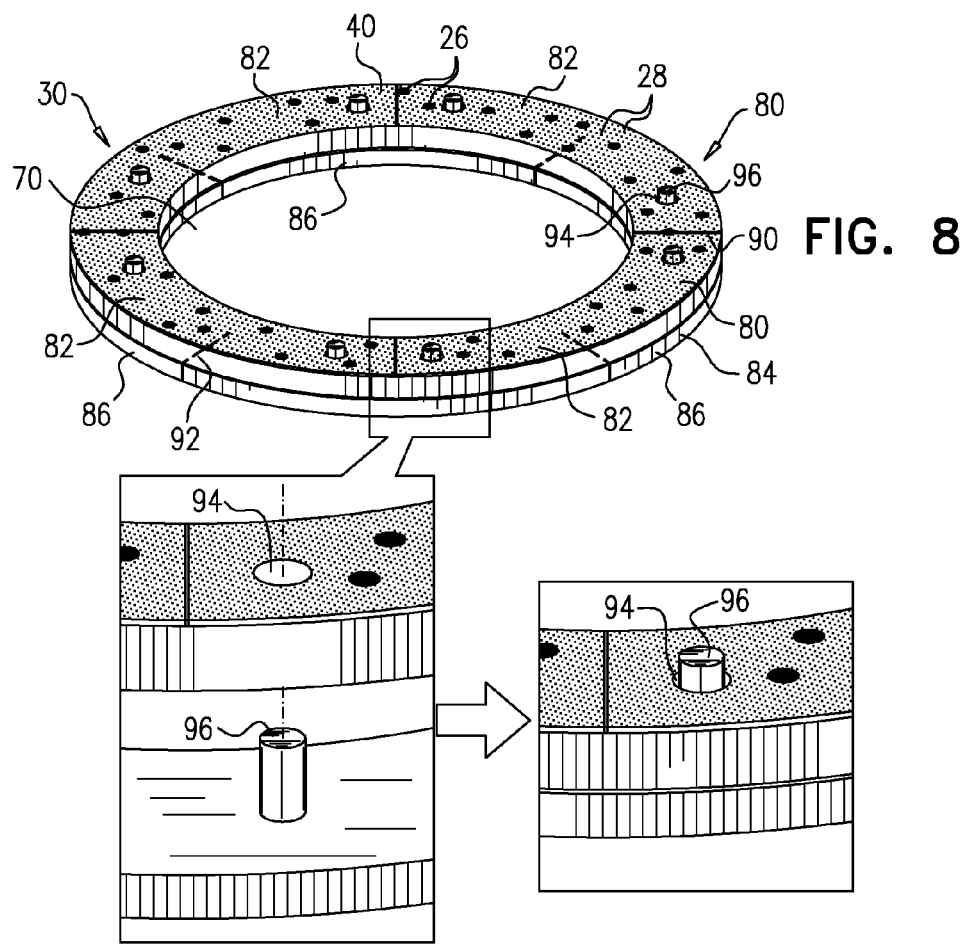
FIG. 8 is a schematic illustration of an alternate configuration of coupling material of the medication-delivery element of FIGS. 7A-C, in accordance with an application of the present invention.

Reference is made to FIG. 8, which is a schematic illustration of an alternate configuration of coupling material 88, in accordance with an application of the present invention. In this configuration, first and second layers 80 and 84 are shaped so as to define a plurality of corresponding holes 94, for example, between two and twenty holes 94. Coupling material 88 is shaped as a plurality of pegs 96, each of which is disposed in a pair of corresponding holes 94 defined by first and second layers 80 and 84, respectively. The pegs thus couple the layers together, until the pegs biodegrade in the small intestine. For example, the pegs may comprise starch. Optionally, the pegs comprise medication 26.

For some applications, the techniques of FIG. 8 are used in configurations in which medication-delivery element 30 is rolled when in the compressed shape 34, such described hereinabove with reference to FIG. 1A or with reference to FIG. 5C, or twisted when in compressed shape 34, such described hereinabove with reference to FIG. 6F.

Figure 9:
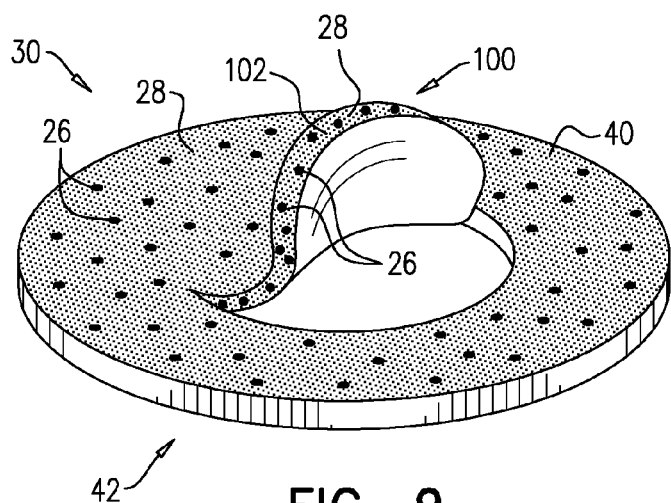
FIG. 9 is a schematic illustration of yet another configuration of the medication-delivery element of the ingestible pill of FIGS. 1A-F, in accordance with an application of the present invention.

Reference is now made to FIG. 9, which is a schematic illustration of yet another configuration of medication-delivery element 30, in accordance with an application of the present invention. In this configuration, a non-border area of medication-delivery element 30 is shaped to define a cut-out flap 100 that includes respective portions of first and second surfaces 40 and 42, each of which portions has an area of at least 10% of the area of space 44 surrounded by outer perimeter P1 of first surface 40, no more than 50% of the area, and/or between 10% and 50% of the area, and/or at least 1 cm2, no more than 6 cm2, and/or between 1 and 6 cm2. Optionally, medication 26 is disposed on a free edge 102 of flap 100. Typically, flap 100 will naturally insert itself into the folds of the small intestine, which may increase surface contact between medication-delivery element 30 and the wall of the small intestine, for better delivery of the medication.

For some applications, medication 26 is disposed on first surface 40 so as to define a plurality of protrusions, each of which has a length of at least 50 microns (e.g., at least 100 microns, such as at least 200 microns), no more than 700 microns (e.g., such as no more than 400 microns, e.g., no more than 300 microns), and/or between 50 (e.g., 100 or 200) and 700 (e.g., 400 or 300) microns, such as 100 microns, 200 microns, or 300 microns. For some applications, a greatest radius of each of the protrusions is at least 20 microns, no more than 100 microns, and/or between 20 and 100 microns. The protrusions are thus sized and shaped to fit well in between the villi of the small intestine, and/or to mesh with the villi, and thus provide high surface area contact between medication 26 and the wall of the small intestine. Optionally, the protrusions are configured to penetrate tissue of the intestinal wall, in order to enhance uptake of medication 26. In addition, the protrusions may function as anchors.

For some applications, medication-delivery element 30 comprises one or more threads, which are configured to intertwine with villi of the small intestine. Typically, medication 26 coats the threads. For some applications, each of at least 90% of the threads has a diameter of between 20 and 50 microns. Alternatively or additionally, for some applications, each of at least 90% of the threads has a length of between 1 and 10 cm, or between 10 and 50 cm. For some applications, the threads are biodegradable.

Figure 10A:
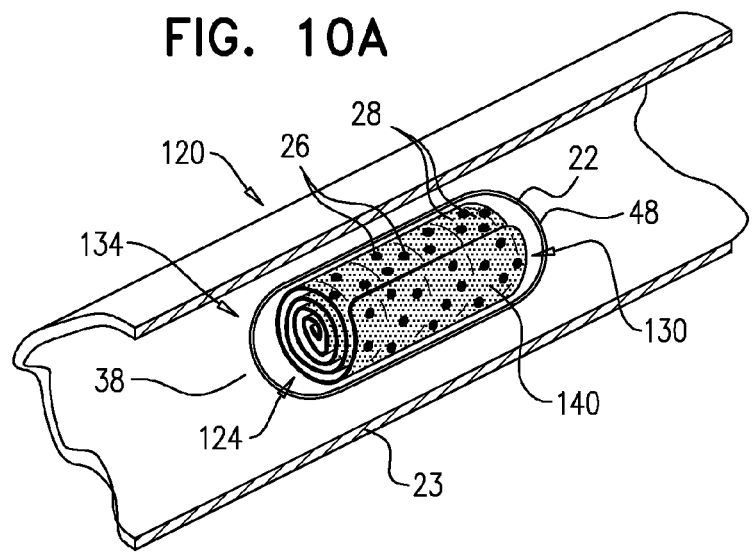
Figure 10B:
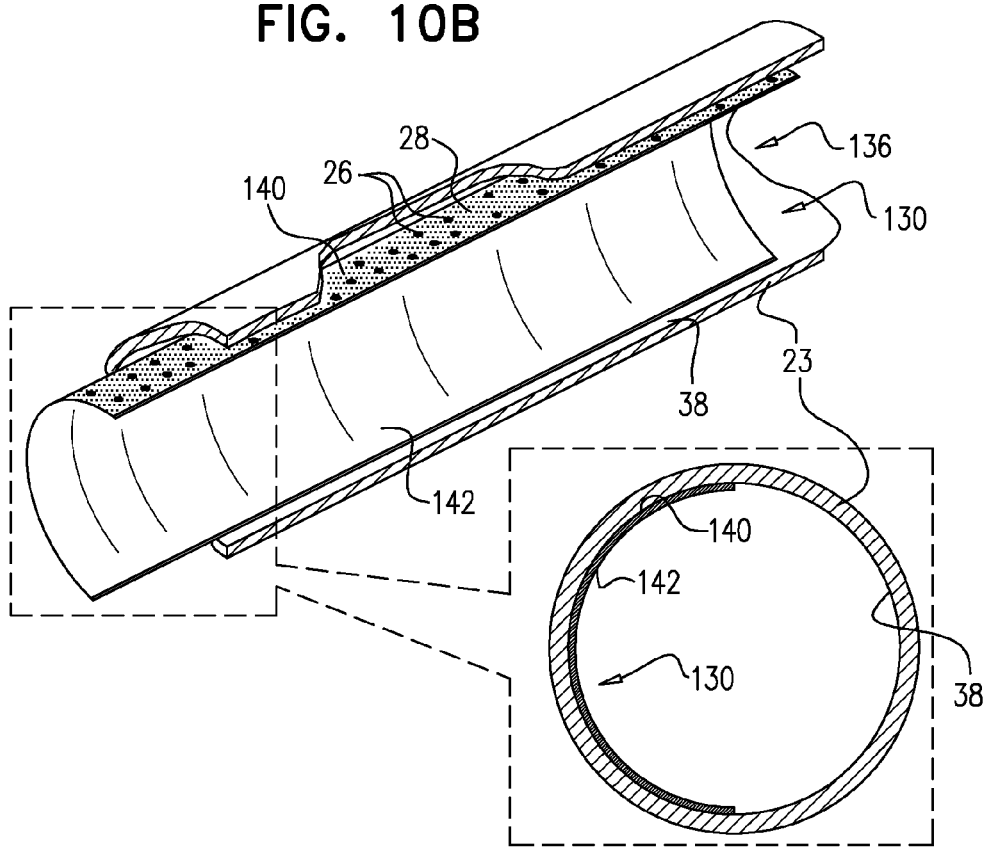

Reference is now made to FIGS. 10A-C, which are schematic illustrations of an ingestible pill 120, for ingestion by a subject, in accordance with an application of the present invention. Ingestible pill 120 incorporates several of the elements of ingestible pill 20, described hereinabove with reference to FIGS. 1A-9, and these elements may implement any of the techniques described hereinabove with reference to FIGS. 1A-9, mutatis mutandis.

Ingestible pill 120 comprises coating 22, as described hereinabove with reference to FIG. 1A, a core 124, medication 26, such as described hereinabove with reference to FIGS. 1A-9, and, optionally, mucoadhesive 28, such as described hereinabove with reference to FIGS. 1A-9. For some applications, as shown in FIG. 10A, pill 120 comprises shell 48, which comprises coating 22. Alternatively, for some applications, core 124 is directly coated with coating 22 (configuration not shown). Typically, pill 120 has a length of at least 5 mm, no more than 30 mm, and/or between 5 and 30 mm before the coating dissolves.

Core 124 comprises an elongate medication-delivery element 130 shaped as a ribbon. Elongate medication-delivery element 130 (a) has a compressed shape 134 when disposed within coating 22, as shown in FIG. 10A, (b) is configured to assume, after coating 22 dissolves, an expanded shape 136, (c) comprises medication 26, and (d) typically has a thickness T2 of less than 0.5 mm (such as less than 0.1 mm), a length L of at least 10 cm, no more than 50 cm, and/or between 10 and 50 cm, and width W2 of at least 0.5 cm, no more than 3 cm, and/or between 0.5 and 3 cm. Elongate medication-delivery element 130 is configured such that medication 26 contacts intestinal wall 38 when elongate medication-delivery element 130 has expanded shape 136. Optionally, core 124 comprises a plurality of elongate medication-delivery elements 130.

FIG. 10B shows elongate medication-delivery element 130 in expanded shape 136, constrained by wall 38 of small intestine 23, while FIG. 10C show elongate medication-delivery element 130 unconstrained in expanded shape 136. Typically, when unconstrained in expanded shape 136, elongate medication-delivery element 130 is rectangular in cross-section perpendicular to a longitudinal axis 152 of elongate medication-delivery element 130 (labeled in FIG. 11), which may facilitate easy rolling of the element into compressed shape 134 for placement within coating 22.

Elongate medication-delivery element 130 is shaped so as to define first and second surfaces 140 and 142 on opposite sides of elongate medication-delivery element 130. Medication 26 at least partially coats first surface 140. For some applications, pill 120 further comprises mucoadhesive 28, which at least partially coats first surface 140. For some applications, mucoadhesive 28 is mixed with medication 26, as symbolically shown in FIGS. 10A-C. Alternatively, for some applications, mucoadhesive 28 is arranged as dots on first surface 140. Further alternatively, medication 26 and mucoadhesive 28 are arranged generally separately on first surface 140, such as described, for example, regarding medication-delivery element 30 with reference to FIG. 1F, mutatis mutandis (for example, mucoadhesive 28 could be disposed in two stripes along the longitudinal borders of elongate medication-delivery element 130, and medication 26 could be disposed between the stripes, farther from the longitudinal borders. For some applications, a non-adhesive material, such as silicone, coats second surface 142, to reduce the likelihood of prolonged contact of second surface 142 with wall 38 of small intestine 23.

For some applications, medication 26 is disposed along at least 75% of a length of elongate medication-delivery element 130, measured along longitudinal axis 152 of elongate medication-delivery element 130 (labeled in FIG. 11).

For some applications, elongate medication-delivery element 130 is rolled when in compressed shape 134 when disposed within coating 22, such as shown in FIG. 10A. For applications in which mucoadhesive 28 is disposed only on first surface 140, rolling the element prevents the mucoadhesive from adhering to itself between turns of the rolled element. Alternatively, elongate medication-delivery element 130 is folded, e.g., in a zigzag shape, a serpentine shape, or a sinusoidal shape, when in compressed shape 134 when disposed within coating 22 (configuration not shown).

Elongate medication-delivery element 130 expands, such as by unrolling and/or unfolding, in response to no longer being constrained by coating 22, and/or in response to contact of core 124 with fluid in the small intestine. Natural peristalsis may aid in such unrolling or unfolding. Once expanded, first surface 140 establishes good (complete or nearly complete) contact with wall 38 of small intestine 23, as shown in FIG. 10B. Factors contributing to this good contact include: (a) the shape and dimensions of medication-delivery element 30, which prevent other, lower-contact-level orientations of the element in the lumen of the small intestine, and (b) the disposition of mucoadhesive 28 on first surface 140, which holds expanded first surface 140 in position during delivery of medication 26, in applications in which the mucoadhesive is provided. Because of this good contact, medication 26 disposed on first surface 140 typically makes contact with intestinal wall 38. This good contact, typically in combination with the high concentration of medication 26 on first surface 140, results in delivery of a high quantity of medication 26 through intestinal wall 38.

Alternatively or additionally, the delivery of the medication through the intestinal wall is enhanced by incorporating a chemical enhancer in the ingestible pill, e.g., by incorporating the chemical enhancer into medication 26. For example, lipophilic molecules may be incorporated into the ingestible pill, which enhance diffusion of the medication across the epithelial layer of the subject's gastrointestinal tract.

Typically, peristalsis has little effect on elongate medication-delivery element 130. Following delivery of medication 26, core 124, including elongate medication-delivery element 130, is passed from the body. For some applications, core 124, including elongate medication-delivery element 130, comprises a biodegradable substance, which biodegrades to facilitate its separation from the wall of the small intestine following delivery of the medication, typically within 1 to 12 hours after the coating dissolves. Alternatively or additionally, core 124 comprises a polymer that absorbs water, expands in the small intestine, and is subsequently broken down by bacteria and/or by the pH found in the colon. In this manner, elongate medication-delivery element 130, which had been substantially enlarged to facilitate drug delivery, decreases in size or otherwise is enabled to separate from the wall of the small intestine or to pass easily from the subject's body. Alternatively, core 124, including elongate medication-delivery element 130, is removed from the body by being passed from the body, without a reduction in size. Thus, as appropriate, the core may be configured to (a) decrease in size in the small intestine, following medication delivery, (b) decrease in size in the colon, or (c) not decrease in size following medication delivery.

For some applications, pill 120 further comprises sodium bicarbonate, which at least partially coats at least one of first and second surfaces 140 and 142, such as surface 140, surface 142, or both surfaces 140 and 142. Upon dissolving of coating 22, the sodium bicarbonate continuously becomes moist, and releases a gas that promotes unrolling of elongate medication-delivery element 130.

Reference is made to FIG. 11, which is a schematic illustration of another configuration of elongate medication-delivery element 130, in accordance with an application of the present invention. In this configuration, elongate medication-delivery element 130 has a plurality of ribs 150. Ribs 150 may help avoid random twisting of elongate medication-delivery element 130 as it unrolls in the small intestine. Optionally, ribs 150 are arched. For some applications, ribs 150 are formed by a thickening of the material of elongate medication-delivery element 130, while for other applications, ribs 150 comprise a material that is fixed to first surface 140 and/or second surface 142 of elongate medication-delivery element 130.

For some applications, ribs 150 are arranged perpendicular to longitudinal axis 152 of elongate medication-delivery element 130, at intervals (I) along the element. For some applications, an average interval is at least 0.5 cm, no more than 2 cm, and/or between 0.5 and 2 cm.

For some applications, elongate medication-delivery element 130 comprises a material selected from the group of materials consisting of: starch and gelatin.

As mentioned above, elongate medication-delivery element 130 typically has thickness T2 of less than 0.5 mm, such as less than 0.1 mm (e.g., between 50 and 100 microns). Such small thicknesses allow elongate medication-delivery element 130 to be rolled and/or folded into a small form for placement in coating 22, despite the relatively long length of the element.

For some applications, medication 26 is disposed on elongate medication-delivery element 130 so as to define a plurality of protrusions, such as described hereinabove regarding medication-delivery element, with reference to FIGS. 1A-9. For some applications, elongate medication-delivery element 130 comprises one or more threads, such as described hereinabove regarding medication-delivery element, with reference to FIGS. 1A-9.

Figure 12A:
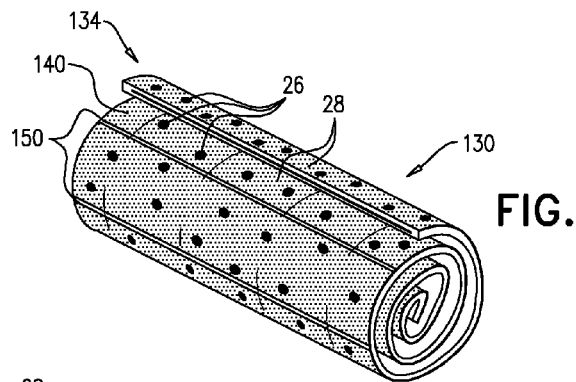
FIGS. 12A-C are schematic illustrations of another configuration of the elongate medication-delivery element of the ingestible pill of FIGS. 10A-C, in accordance with an application of the present invention.
Figure 12B:
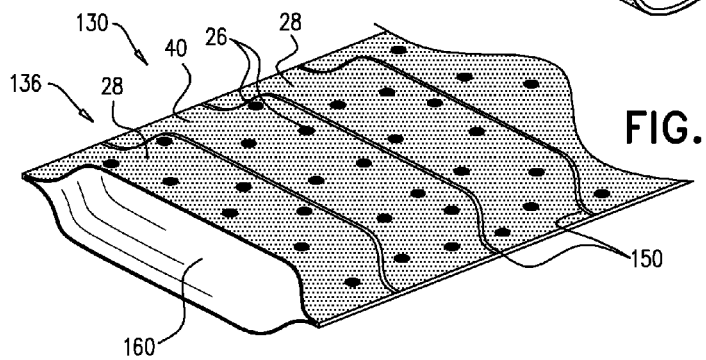
Figure 12C:
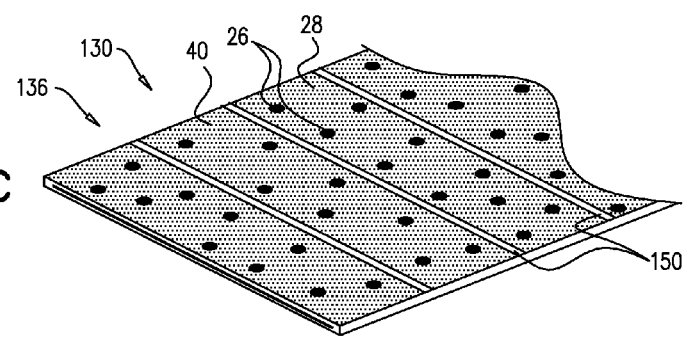

Reference is made to FIGS. 12A-C, which are schematic illustrations of another configuration of elongate medication-delivery element 130, in accordance with an application of the present invention. In this configuration, elongate medication-delivery element 130 is inflatable, and is configured to transition from compressed shape 134 to expanded shape 136 upon inflation.

FIG. 12A shows elongate medication-delivery element 130 rolled in compressed shape 134 (alternatively or additionally, the element may be folded when in compressed shape 134).

Inflation of elongate medication-delivery element 130 (i.e., of one or more chambers 160 thereof), as shown in FIG. 12B, transitions the element to expanded shape 136, such as shown in FIG. 12B, such as by unrolling (and/or unfolding).

As shown in FIG. 12C, for some applications, elongate medication-delivery element 130 deflates soon after unrolling, and assumes a shape that is flat and non-circular in cross-section. For some applications, ribs 150 facilitate such deflation. Alternatively, elongate medication-delivery element 130 remains slightly inflated upon deployment, and ribs 150 hold the element fairly flat (flatter than shown in FIG. 12B) while inflated; in this case, the element does not necessarily achieve the deflated state shown in FIG. 12C.

Figure 13:
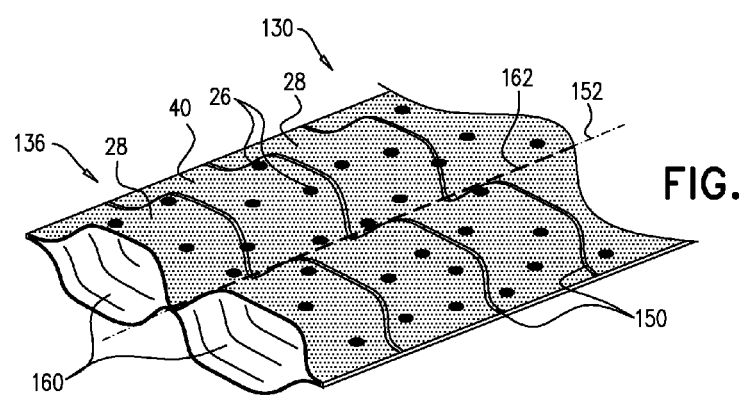
FIG. 13 is a schematic illustration of yet another configuration of the elongate medication-delivery element of the ingestible pill of FIGS. 10A-C, in accordance with an application of the present invention.

Reference is made to FIG. 13, which is a schematic illustration of yet another configuration of elongate medication-delivery element 130, in accordance with an application of the present invention. In this configuration, elongate medication-delivery element 130 is inflatable, as described hereinabove with reference to FIGS. 12A-C, and comprises one or more elongate dividers 162 (e.g., seams) aligned longitudinally along elongate medication-delivery element 130 (typically parallel to longitudinal axis 152 thereof). Dividers 162 at least partially divide an interior of the inflatable element into a plurality of longitudinal chambers 160. The dividers thus maintain elongate medication-delivery element 130 fairly flat even during inflation; in this case, the element does not necessarily achieve the deflated states shown in FIG. 12C. Dividers 162 may be generally continuous along medication-delivery element 130, or may comprise point or short segments of fixation between opposite sides of the inflatable element.

Reference is now made to FIGS. 14A-D, which are schematic illustrations of an ingestible pill 220, for ingestion by a subject, in accordance with an application of the present invention. Ingestible pill 220 incorporates several of the elements of ingestible pill 20, described hereinabove with reference to FIGS. 1A-9, and these elements may implement any of the techniques described hereinabove with reference to FIGS. 1A-9, mutatis mutandis.

Figure 14A:
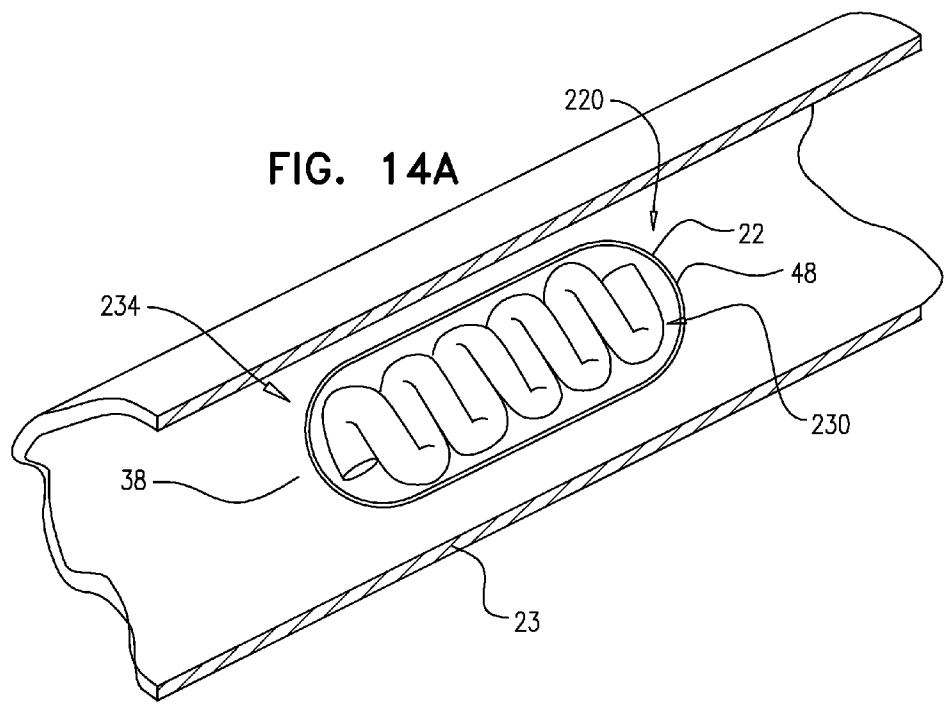
FIGS. 14A-D are schematic illustrations of yet another ingestible pill, for ingestion by a subject, in accordance with an application of the present invention.

Ingestible pill 220 comprises coating 22, as described hereinabove with reference to FIG. 1A, a core 224, medication 26, such as described hereinabove with reference to FIGS. 1A-9, and, optionally, mucoadhesive 28, such as described hereinabove with reference to FIGS. 1A-9. For some applications, as shown in FIG. 14A, pill 220 comprises shell 48, which comprises coating 22. Alternatively, for some applications, core 224 is directly coated with coating 22 (configuration not shown). Typically, pill 220 has a length of at least 5 mm, no more than 30 mm, and/or between 5 and 30 mm before the coating dissolves.

Figure 14B:
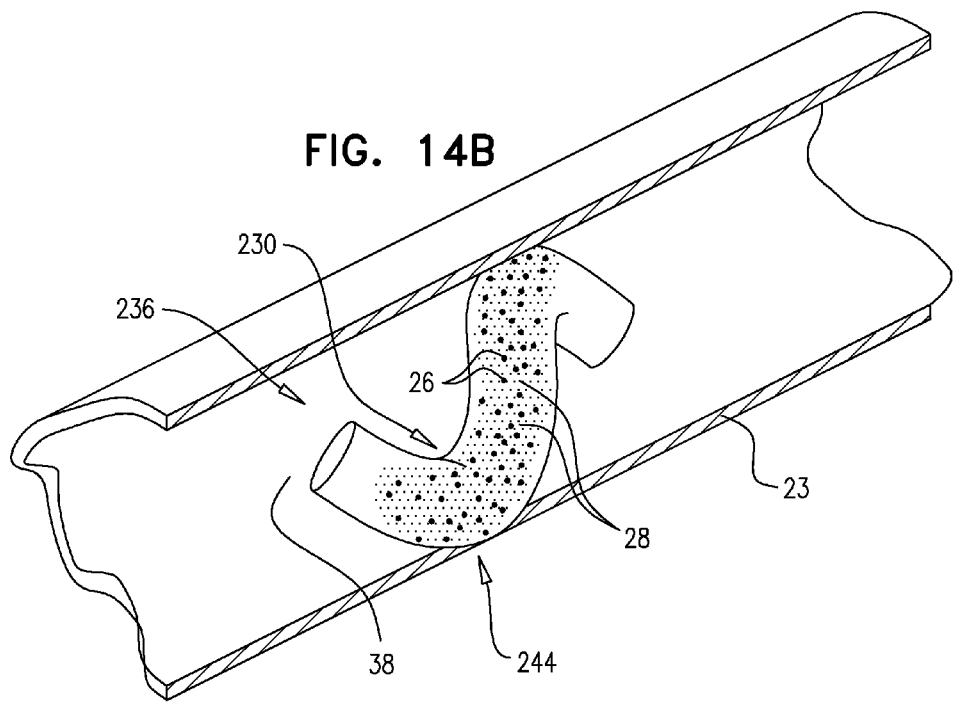
Figure 14C:
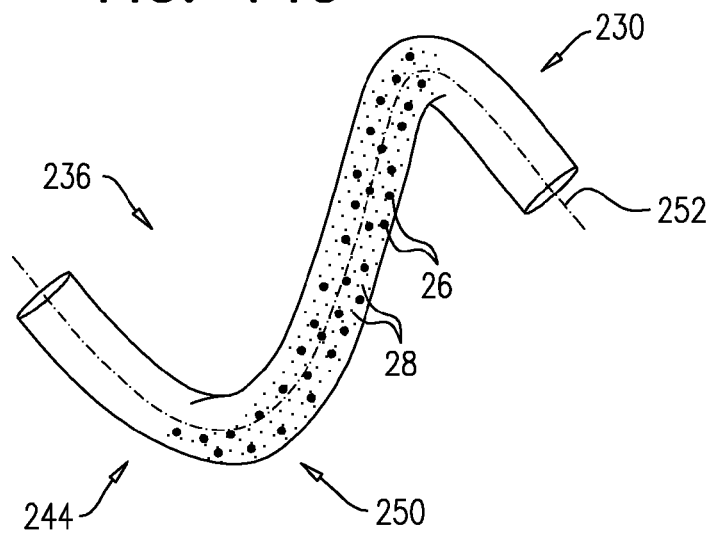

Core 224 comprises an elongate medication-delivery element 230 having an outer surface 240 and a longitudinal axis 252 (labeled in FIG. 14C). Elongate medication-delivery element 230 (a) has a compressed shape 234 when disposed within coating 22, (b) is configured to assume, after coating 22 dissolves, an expanded shape 236 of a three-dimensional space curve 244, and (c) comprises medication 26. Outer surface 240 is configured such that medication 26 contacts intestinal wall 38 when elongate medication-delivery element 230 has expanded shape 236. Optionally, core 224 comprises a plurality of elongate medication-delivery elements 230.

Figure 14D:
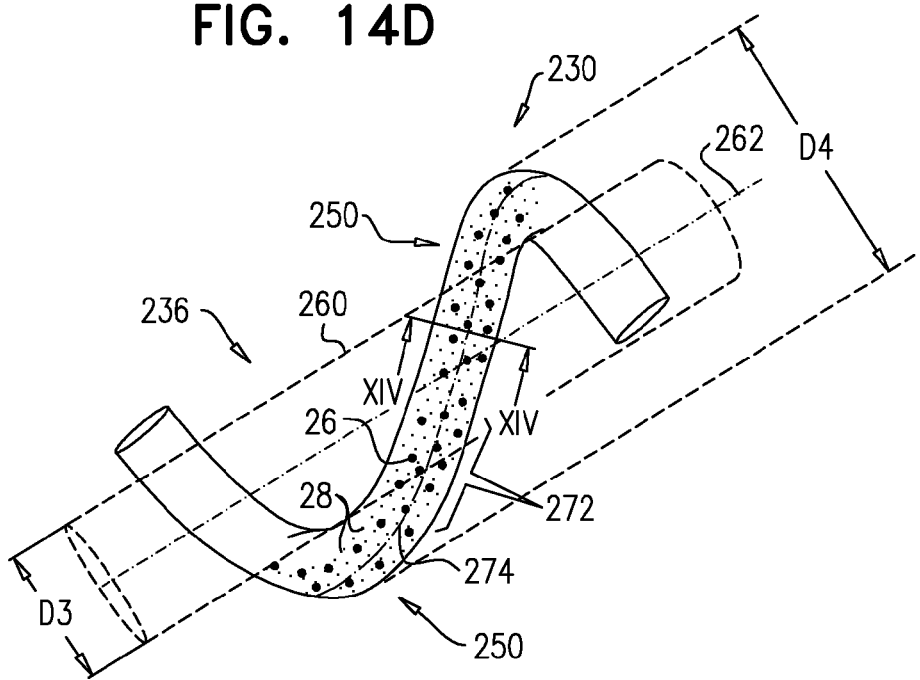

FIG. 14B shows elongate medication-delivery element 230 in expanded shape 236, constrained by wall 38 of small intestine 23, while FIGS. 14C-D show elongate medication-delivery element 230 unconstrained in expanded shape 136. For some applications, medication 26 is disposed on, e.g., at least partially coats, outer surface 240, e.g., is printed on the outer surface. For some applications, when elongate medication-delivery element 230 has expanded shape 236 and is unconstrained, outer surface 240 of elongate medication-delivery element 230 has a surface area, and the medication is disposed on less than 50% of the surface area.

For some applications, medication 26 is disposed on outer surface 240, and elongate medication-delivery element 230 is configured such that when elongate medication-delivery element 230 has expanded shape 236, medication 26 disposed on outer surface 240 contacts intestinal wall 38 providing 360 degrees of contact of medication 26 with intestinal wall 38. Alternatively or additionally, for some applications, elongate medication-delivery element 230 is configured such that when elongate medication-delivery element 230 has expanded shape 236 and is disposed in a circular cylinder having an inner diameter of 2.5 cm, the medication disposed on outer surface 240 has 360 degrees of contact with an inner surface of the cylinder. (It is to be understood that the cylinder is not a component of pill 220, but instead is used conceptually to define a structural property of the pill independent of its use in the small intestine.)

For some applications, the medication is disposed along at least 75% of a length of elongate medication-delivery element 230, measured along longitudinal axis 252 of elongate medication-delivery element 230, when elongate medication-delivery element 230 has expanded shape 236 and is unconstrained.

For some applications, pill 220 further comprises mucoadhesive 28, which at least partially coats outer surface 240. For some applications, mucoadhesive 28 is mixed with medication 26, as symbolically shown in FIGS. 14B-C. Alternatively, for some applications, mucoadhesive 28 is arranged as dots on outer surface 240. For some applications, a non-adhesive material, such as silicone, coats at least a portion of outer surface 240 not coated by mucoadhesive 28, to reduce the likelihood of prolonged contact of this non-mucoadhesive-coated surface with wall 38 of small intestine 23.

For some applications, elongate medication-delivery element 230 comprises a sponge, i.e., a soft, light porous substance, which is configured to expand in the small intestine when released from coating 22, optionally upon absorbing a fluid of the small intestine. In addition, the use of a sponge may avoid putting any rigid materials against the villi and/or folds of the wall of the small intestine. For some applications, the sponge comprises gelatin and/or polyurethane. For some applications, the sponge is biodegradable in whole or in part (typically within 1 to 12 hours after the coating dissolves), while for other applications the sponge is not biodegradable. For some applications, medication 26 comprises a liquid that is absorbed in the sponge.

For some applications, such as shown in FIGS. 14C-D, at least 50% (e.g., at least 75%, such as 100%) of a length of elongate medication-delivery element 230, measured along longitudinal axis 252 of elongate medication-delivery element 230, is shaped as a helix 250 when elongate medication-delivery element 230 has expanded shape 236 and is unconstrained. Typically, helix 250 has at least 0.75 helix turns when elongate medication-delivery element 230 has expanded shape 236 and is unconstrained, such as at least one helix turn, e.g., at least two helix turns. For some applications, helix 250 has no more than three helix turns when elongate medication-delivery element 230 has expanded shape 236 and is unconstrained. (It is noted that longitudinal axis 252 is typically not straight, but instead has the longitudinal shape of elongate medication-delivery element 230, such as labeled in FIG. 14C.)

For some applications, as shown in FIG. 14D, when elongate medication-delivery element 230 has expanded shape 236 and is unconstrained, helix 250 radially surrounds a cylindrical space 260 having a diameter D3 perpendicular to a longitudinal axis 262 of cylindrical space 260 of at least 3 cm, no more than 7 cm, and/or between 3 and 7 cm. This relatively large space allows free passage of the contents of the small intestine through the helix.

For some applications, helix 250 is a circular helix when elongate medication-delivery element 230 has expanded shape 236 and is unconstrained. For some applications, helix 250 has an outer diameter D4 of at least 4 cm, no more than 7 cm, and/or between 4 and 7 cm when elongate medication-delivery element 230 has expanded shape 236 and is unconstrained.

For some applications, elongate medication-delivery element 230 has a length, measured along longitudinal axis 252 of elongate medication-delivery element 230, of at least 10 cm, no more than 50 cm, and/or between 10 and 50 cm when elongate medication-delivery element 230 has expanded shape 236 and is unconstrained.

For some applications, compressed shape 134 is selected from the group of shapes consisting of: a serpentine shape, a sinusoidal shape, a zigzag shape, or another folded shape when disposed within coating 22, such as shown in FIG. 14A. Alternatively, compressed shape 134 may be helical. These shapes may enable elongate medication-delivery element 230 to spontaneously transition to expanded shape 236 upon release from coating 22. Alternatively or additionally, elongate medication-delivery element 230 is rolled when in the compressed shape.

Elongate medication-delivery element 230 expands, such as by unfolding and/or unrolling, in response to no longer being constrained by coating 22, and/or in response to contact of core 224 with fluid in the small intestine. Natural peristalsis may aid in such unrolling or unfolding. Once expanded, a radially-outwardly-directed portion of outer surface 240 establishes good (complete or nearly complete) contact with wall 38 of small intestine 23, as shown in FIG. 14B. Factors contributing to this good contact include: (a) the shape and dimensions of medication-delivery element 30, which prevent other, lower-contact-level orientations of the element in the lumen of the small intestine, and (b) the disposition of mucoadhesive 28 on the radially-outwardly-directed portion of outer surface 240, which holds the radially-outwardly-directed portion of the expanded outer surface 240 in position during delivery of medication 26, in applications in which the mucoadhesive is provided. Because of this good contact, medication 26 disposed on the radially-outwardly-directed portion of outer surface 240 typically makes contact with intestinal wall 38. This good contact, typically in combination with the high concentration of medication 26 on outer surface 240, results in delivery of a high quantity of medication 26 through intestinal wall 38.

Alternatively or additionally, the delivery of the medication through the intestinal wall is enhanced by incorporating a chemical enhancer in the ingestible pill, e.g., by incorporating the chemical enhancer into medication 26. For example, lipophilic molecules may be incorporated into the ingestible pill, which enhance diffusion of the medication across the epithelial layer of the subject's gastrointestinal tract.

Following delivery of medication 26, core 224, including elongate medication-delivery element 230, is passed from the body. For some applications, core 224, including elongate medication-delivery element 230, comprises a biodegradable substance, which biodegrades to facilitate its separation from intestinal wall 38 following delivery of the medication, typically within 1 to 12 hours after the coating dissolves. Alternatively or additionally, core 224 comprises a polymer that absorbs water, expands in the small intestine, and is subsequently broken down by bacteria and/or by the pH found in the colon. In this manner, elongate medication-delivery element 230, which had been substantially enlarged to facilitate drug delivery, decreases in size or otherwise is enabled to separate from intestinal wall 38 or to pass easily from the subject's body. Alternatively, core 224, including elongate medication-delivery element 230, is removed from the body by being passed from the body, without a reduction in size. Thus, as appropriate, the core may be configured to (a) decrease in size in the small intestine, following medication delivery, (b) decrease in size in the colon, or (c) not decrease in size following medication delivery. For some applications, elongate medication-delivery element 230 is configured to break apart in the small intestine, e.g., components of the element are glued together with biodegradable glue.

Figure 15:
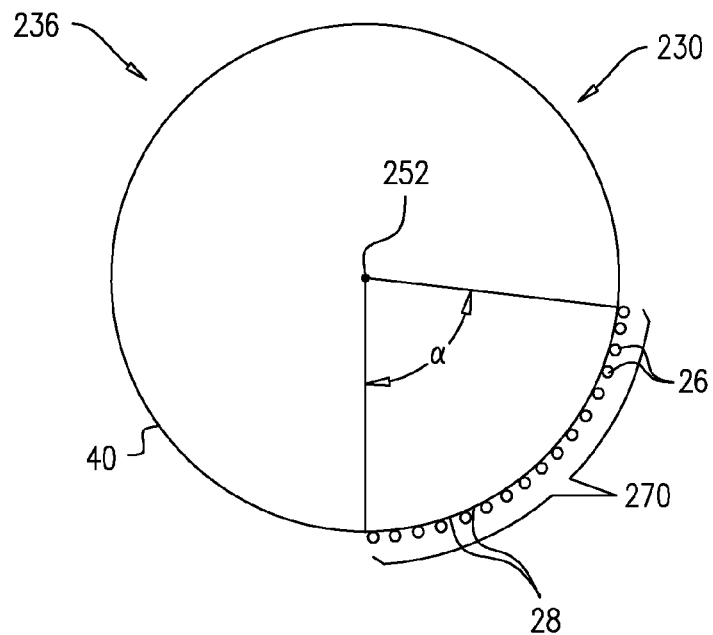
FIG. 15 is a schematic cross-sectional view of an elongate medication-delivery element of the ingestible pill of FIGS. 14A-D in an expanded shape, in accordance with an application of the present invention.

Reference is made to FIGS. 14C-D, as well as FIG. 15, which is a schematic cross-sectional view of elongate medication-delivery element 230 in expanded shape 236, in accordance with an application of the present invention. In this configuration, when elongate medication-delivery element 230 has expanded shape 236 and is unconstrained, medication 26 is disposed on outer surface 240 of elongate medication-delivery element 230 around a circumferential portion 270 of elongate medication-delivery element 230 at least along a longitudinal segment 272 of elongate medication-delivery element 230. Circumferential portion 270 subtends an angle α (alpha) of at least 45 degrees, no more than 135 degrees, and/or between 45 and 135 degrees, such as at least 75 degrees, no more than 105 degrees, and/or between 75 and 105 degrees. Longitudinal segment 272 has a length of at least 1 cm, measured along longitudinal axis 252 of elongate medication-delivery element 230. Circumferential portion 270, at all locations along longitudinal segment 272, includes a radially-outermost surface 274 of helix 250.

For some applications, a circumferential orientation of circumferential portion 270 varies along longitudinal segment 272.

For some applications, pill 220 further comprises mucoadhesive 28 coated on a portion of outer surface 240 of elongate medication-delivery element 230 at which the medication is disposed.

Reference is made to FIG. 15. For some applications, elongate medication-delivery element 230 has an average cross-sectional area perpendicular to longitudinal axis 252 of elongate medication-delivery element 230 of at least 7 mm2, no more than 80 mm2 (e.g., no more than 30 mm2, and/or between 7 and 80 mm2, such as between 7 and 30 mm2, when elongate medication-delivery element 230 has expanded shape 236 and is unconstrained.

For some applications, elongate medication-delivery element 230 has an average compressed cross-sectional area perpendicular to longitudinal axis 252 of elongate medication-delivery element 230 when elongate medication-delivery element 230 has compressed shape 234, such as shown in FIG. 14A, and an average expanded cross-sectional area perpendicular to longitudinal axis 252 when elongate medication-delivery element 230 has expanded shape 236 and is unconstrained, such as shown in FIGS. 14C-D and 15. The average expanded cross-sectional area is greater than the average compressed cross-sectional area. For example, the average expanded cross-sectional area may be at least 300%, such as at least 500%, of the average compressed cross-sectional area. For some applications, elongate medication-delivery element 230 is configured to transition from the average compressed cross-sectional area to the average expanded cross-sectional area by absorbing a fluid. For some applications, elongate medication-delivery element 230 comprises a material that is configured to generate a gas when exposed to the fluid.

For some applications, elongate medication-delivery element 230 has a non-circular cross-sectional shape (e.g., an elliptical cross-sectional shape) perpendicular to longitudinal axis 252 of elongate medication-delivery element 230 when elongate medication-delivery element 230 has the compressed shape, and a circular cross-sectional shape perpendicular to longitudinal axis 252 when elongate medication-delivery element 230 has expanded shape 236 and is unconstrained, such as shown in FIG. 15.

Figure 16:
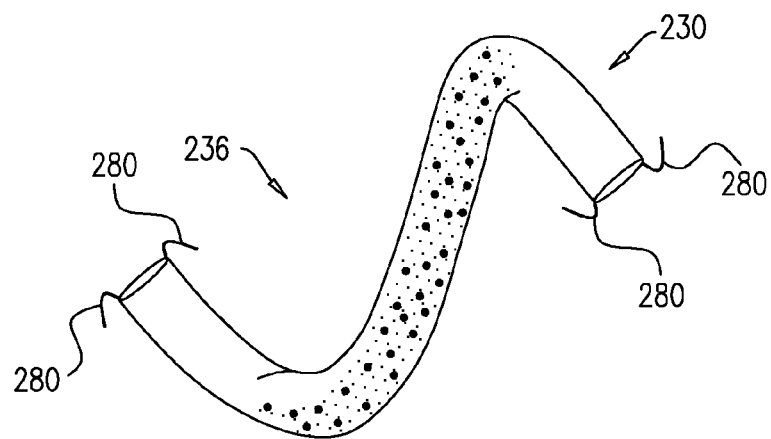
FIG. 16 is a schematic illustration of another configuration of the elongate medication-delivery element of the ingestible pill of FIGS. 14A-D, in accordance with an application of the present invention.

Reference is made to FIG. 16, which is a schematic illustration of another configuration of elongate medication-delivery element 230, in accordance with an application of the present invention. In this configuration, elongate medication-delivery element 230 comprises one or more anchors 280, which are configured to anchor elongate medication-delivery element 230 to intestinal wall 38. Such anchoring may help the elongate medication-delivery element stretch out in the small intestine, thereby increasing contact of the medication with intestinal wall 38. For some applications, anchors 280 are dissolvable. For some applications, anchors 280 are shaped as claws. For some applications, one or more of anchors 280 are disposed at or near one or both ends of elongate medication-delivery element 230, as shown. Alternatively, one or more of anchors 280 are disposed elsewhere along element 230 (configuration not shown).

For some applications, medication 26 is disposed on elongate medication-delivery element 230 so as to define a plurality of protrusions, such as described hereinabove regarding medication-delivery element, with reference to FIGS. 1A-9. For some applications, elongate medication-delivery element 230 comprises one or more threads, such as described hereinabove regarding medication-delivery element, with reference to FIGS. 1A-9.

Reference is now made to FIGS. 1A-9 and FIGS. 14A-16. In some applications of the present invention, an ingestible pill comprises coating 22, configured to dissolve in an small intestine of the subject; and a core, which comprises a sponge, which (a) has a compressed shape and compressed volume when disposed within coating 22, (b) is configured to assume, after coating 22 dissolves, an expanded shape and an expanded volume, the expanded volume at least 3 times (such as at least 5 times) the compressed volume, and (c) comprises medication 26 and mucoadhesive 28. These applications of the present invention may incorporate any of the features described hereinabove with reference to FIGS. 1A-9 or FIGS. 14A-16, mutatis mutandis.

For some applications, the core comprises medication-delivery element 30, described hereinabove with reference to FIGS. 1A-9. Alternatively, for some applications, the core comprises medication-delivery element 230, described hereinabove with reference to FIGS. 14A-16. Further alternatively, the core comprises another medication-delivery element.

For some applications, mucoadhesive 28 is disposed on a portion of an outer surface of the sponge, which outer surface is configured such that mucoadhesive 28 contacts intestinal wall 38 when the sponge has the expanded shape. Alternatively or additionally, for some applications, medication 26 is disposed on at least a portion of the outer surface of the sponge, which outer surface is configured such that medication 26 contacts intestinal wall 38 when the sponge has the expanded shape. For some applications, when the sponge has the expanded shape and is unconstrained, the outer surface of the sponge has a surface area, and the medication is disposed on less than 50% of the surface area.

For some applications, when the sponge has the expanded shape and is unconstrained, the mucoadhesive is disposed on less than 50% of the surface area.

For some applications, when the sponge has the expanded shape and is unconstrained, more of the mucoadhesive is disposed on one side of the sponge than on another side of the sponge.

For some applications, medication 26 is disposed on the sponge so as to define a plurality of protrusions, such as described hereinabove regarding medication-delivery element 30, with reference to FIGS. 1A-9. For some applications, the medication-delivery element comprises one or more threads, such as described hereinabove regarding medication-delivery element 30, with reference to FIGS. 1A-9.

Figure 17:
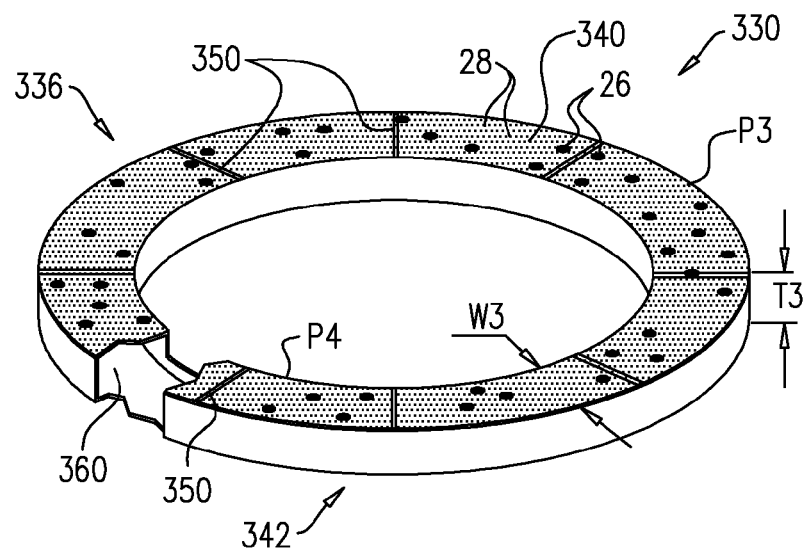
FIG. 17 is a schematic illustration of a medication-delivery ring, in accordance with an application of the present invention.

Reference is now made to FIG. 17, which is a schematic illustration of a medication-delivery ring 330, in accordance with an application of the present invention. Medication-delivery ring 330 is delivered to the small intestine in an ingestible pill such as pill 20, described hereinabove with reference to FIGS. 1A-9, optionally using the folding and rolling technique described hereinabove with reference to FIGS. 5A-C, or the folding and twisting technique described hereinabove with reference to FIGS. 6A-F. The ingestible pill of this application incorporates several of the elements of ingestible pill 20, described hereinabove with reference to FIGS. 1A-9, and these elements may implement any of the techniques described hereinabove with reference to FIGS. 1A-9, mutatis mutandis.

A core of the pill comprises medication-delivery ring 330, which (a) has a compressed shape when disposed within coating 22, (b) is configured to assume, after coating 22 dissolves, an expanded shape 336, and (c) comprises medication 26. When medication-delivery ring 330 is unconstrained in expanded shape 336, the medication-delivery ring has (a) an outer perimeter P3 of at least 6 cm, no more than 30 cm, and/or between 6 and 30 cm, and (b) a thickness T3, measured in a direction perpendicular to a plane defined by the outer perimeter, of less than 0.5 cm, such as less than 0.3 cm. Medication-delivery ring 330 is configured such that medication 26 contacts intestinal wall 38 when medication-delivery ring 330 has expanded shape 336. Optionally, the core of the pill comprises a plurality of medication-delivery rings 330.

The relatively flat and large shape of medication-delivery ring 330 results in the ring wrapping around a portion of intestinal wall 38, with good contact with the wall, such as shown for medication-delivery element 30 in FIG. 1B. In contrast, if shaped as a conventional o-ring, and with no further modifications, medication-delivery element 330 would not align properly against the wall of the small intestine. (When a conventional o-ring is squeezed on radially-opposite sides, e.g., at 12 o'clock and 6 o'clock, the o-ring may remain in plane or assume an unpredictable, arbitrary three-dimensional shape. In contrast, when the present configuration of medication-delivery element 330 is squeezed on radially-opposite sides by the intestinal wall, the relatively large width W1 causes the element to assume the desired shape, which properly aligns with the intestinal wall, as shown for medication-delivery element 30 in FIG. 1B.)

For some applications, when medication-delivery ring 330 is unconstrained in the expanded shape, an average width W3 of medication-delivery ring 330, measured between outer perimeter P3 of medication-delivery ring 330 and an inner perimeter P4 of medication-delivery ring 330, equals at least 3 times thickness T3, no more than 8 times thickness T3, and/or between 3 and 8 times thickness T3, and/or at least 3 mm, no more than 12 mm, and/or between 3 and 12 mm.

For some applications, medication-delivery ring 330 is shaped so as to define first and second surfaces 340 and 342 on opposite sides of medication-delivery ring 330, and wherein medication 26 at least partially coats first surface. For some applications, the pill further comprises mucoadhesive 28, which at least partially coats first surface 340. The ring may incorporate features of the medication and the mucoadhesive described hereinabove with reference to FIGS. 1A-16.

For some applications, medication-delivery ring 330 is inflatable and is shaped so as to define at least one internal chamber 360. Medication-delivery ring 330 is shown inflated in FIG. 17, and uninflated in FIG. 18. Medication-delivery ring 330 is uninflated when in the compressed shape when disposed within coating 22, and medication-delivery ring 330 is configured to assume expanded shape 336 upon inflation. For some applications, medication-delivery ring 330 comprises radial ribs 350, which are configured to prevent over-inflation.

For some applications, medication-delivery ring 330 further comprises sodium bicarbonate, and a substance, such as an acid (e.g., citric acid), or water, typically disposed in the at least one internal chamber 360.

Figure 18:
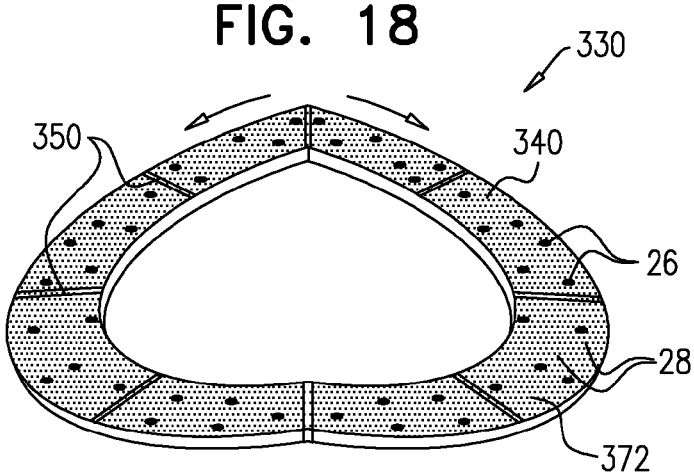
FIG. 18 is a schematic illustration of the medication-delivery ring of FIG. 17 partially folded, in accordance with an application of the present invention.

Reference is made to FIG. 18, which is a schematic illustration of medication-delivery ring 330 partially folded, in accordance with an application of the present invention.

For some applications, when in the compressed shape, medication-delivery ring 330 is folded into at least first and second segments 370 and 372. Although the ring is typically completely folded, for clarity of illustration the ring is shown only partially folded in FIG. 18. After being folded, the ring may additionally be rolled, such as described hereinabove with reference to FIGS. 5A-C, mutatis mutandis, or may additionally be twisted, such as described hereinabove with reference to FIGS. 6A-F, mutatis mutandis.

The substance (e.g., the acid, or the water) is disposed in medication-delivery ring 330 in first segment 370, and the sodium bicarbonate is disposed in medication-delivery ring 330 in the second segment. Because of the fold, there is minimal or no contact between the substance and the sodium bicarbonate until the ring unfolds upon release from coating 22 in the small intestine. Contact between the substance and the sodium bicarbonate generates a gas, which inflates medication-delivery ring 330.

For some applications, medication-delivery ring 330 comprises an elastomer, such as silicone. Alternatively, for some applications, medication-delivery ring 330 comprises a sponge, for example as described hereinabove.

For some applications, medication-delivery ring 330 is biodegradable in the small intestine, typically within 1 to 12 hours after the coating dissolves; for example, the ring may comprise a starch.

For some applications, the techniques described herein are practiced in combination with techniques described in U.S. Pat. No. 8,247,902 to Gross, which is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an ingestible pill, which comprises:
   a coating configured to dissolve in a small intestine of a subject;
   a core, which comprises a medication-delivery element, which (a) has a compressed shape when disposed within the coating, and (b) is configured to assume, after the coating dissolves, an expanded shape;
   a medication; and
   a mucoadhesive,
   wherein, when the medication-delivery element is unconstrained in the expanded shape:
      the medication-delivery element is shaped so as to define first and second surfaces on opposite sides of the medication-delivery element, which first and second surfaces have respective outer perimeters, which surround respective spaces of the respective surfaces, which spaces have respective greatest dimensions equal to between 2 and 10 cm, and each of which spaces has an area equal to at least 50% of the square of the greatest dimension thereof, and
      the medication-delivery element has an average thickness between the first and the second surfaces of less than 6 mm, and
   wherein each of the medication and the mucoadhesive at least partially coats the first surface.

2. The apparatus according to claim 1, wherein the area of each of the spaces is equal to at least 75% of the square of the greatest dimension thereof.

3. The apparatus according to claim 1, wherein the greatest dimensions are at least 3 cm.

4. The apparatus according to claim 1, wherein the medication-delivery element, when unconstrained in the expanded shape, is generally flat.

5. The apparatus according to claim 1, wherein at least 90% of the mucoadhesive, by weight, is disposed on the first surface.

6. The apparatus according to claim 1, wherein at least 90% of the medication, by weight, is disposed on the first surface.

7. The apparatus according to claim 1, wherein at least 75% of the first surface faces at least partially radially outwardly, when the medication-delivery element has the compressed shape when disposed within the coating.

8. The apparatus according to claim 1, wherein the average thickness is at least 1 mm when the medication-delivery element is unconstrained in the expanded shape.

9. The apparatus according to claim 1, wherein the average thickness is less than 4 mm when the medication-delivery element is unconstrained in the expanded shape.

10. The apparatus according to claim 1, wherein the medication-delivery element comprises a biodegradable polymer mixed with a flexible material.

11. The apparatus according to claim 1, wherein the medication-delivery element, when unconstrained in the expanded shape, is shaped so as to define one or more openings therethrough.

12. The apparatus according to claim 11, wherein the medication-delivery element, when unconstrained in the expanded shape, is shaped so as to define a plurality of openings therethrough.

13. The apparatus according to claim 12, wherein an aggregate area of the plurality of openings equals at least 10% of the area of the space surrounded by the outer perimeter of the first surface, when the medication-delivery element is unconstrained in the expanded shape.

14. The apparatus according to claim 12, wherein an average area of the plurality of openings equals at least 0.5% of the area of the space surrounded by the outer perimeter of the first surface, when the medication-delivery element is unconstrained in the expanded shape.

15. The apparatus according to claim 11, wherein an area of one of the one or more openings equals between 25% and 90% of the area of the space surrounded by the outer perimeter of the first surface, when the medication-delivery element is unconstrained in the expanded shape.

16. The apparatus according to claim 15, wherein the area of the one of the one or more openings equals between 50% and 85% of the area of the space surrounded by the outer perimeter of the first surface, when the medication-delivery element is unconstrained in the expanded shape.

17. The apparatus according to claim 15, wherein an average width of the medication-delivery element, measured between the outer perimeter of the first surface and the one of the one or more openings, equals at least 3 times the average thickness, when the medication-delivery element is unconstrained in the expanded shape.

18. The apparatus according to claim 15, wherein, when the medication-delivery element has the compressed shape, the medication-delivery element is in a folded configuration that is rolled.

19. The apparatus according to claim 15, wherein, when the medication-delivery element has the compressed shape, the medication-delivery element is in a folded configuration that is twisted.

20. A method of administration of a medication to a subject, the method comprising:
receiving, by the subject, an ingestible pill, which includes (i) a coating configured to dissolve in a small intestine of the subject, (ii) a core, which includes a medication-delivery element, which (a) has a compressed shape when disposed within the coating, and (b) is configured to assume, after the coating dissolves, an expanded shape, (iii) the medication, and (iv) a mucoadhesive; and
swallowing the ingestible pill by the subject, so that the coating dissolves in the small intestine and the medication-delivery element assumes the expanded shape,
wherein, when the medication-delivery element is unconstrained in the expanded shape:
the medication-delivery element is shaped so as to define first and second surfaces on opposite sides of the medication-delivery element, which first and second surfaces have respective outer perimeters, which surround respective spaces of the respective surfaces, which spaces have respective greatest dimensions equal to between 2 and 10 cm, and each of which spaces has an area equal to at least 50% of the square of the greatest dimension thereof, and
the medication-delivery element has an average thickness between the first and the second surfaces of less than 6 mm, and
wherein each of the medication and the mucoadhesive at least partially coats the first surface.

21. The method according to claim 20, wherein at least 90% of the mucoadhesive, by weight, is disposed on the first surface.

22. The method according to claim 20, wherein at least 90% of the medication, by weight, is disposed on the first surface.

23. The method according to claim 20, wherein receiving the ingestible pill comprises receiving the ingestible pill in which at least 75% of the first surface faces at least partially radially outwardly, when the medication-delivery element has the compressed shape when disposed within the coating.

24. The method according to claim 20, wherein the average thickness is less than 4 mm when the medication-delivery element is unconstrained in the expanded shape.

25. The method according to claim 20, wherein the medication-delivery element, when unconstrained in the expanded shape, is shaped so as to define one or more openings therethrough.

26. The apparatus according to claim 1, wherein the coating is pH-sensitive, and is configured to dissolve within 10 minutes only within a range of pH values, which range has a low end of between 6.5 and 8.5.

27. The apparatus according to claim 7, wherein at least 90% of the medication, by weight, is disposed on the first surface.

28. The apparatus according to claim 7, wherein at least 90% of the mucoadhesive, by weight, is disposed on the first surface.

29. The apparatus according to claim 15, wherein the area of the one of the one or more openings is at least 2.5 $cm^2$.

* * * * *